United States Patent [19]
Ohi et al.

[11] Patent Number: 5,683,893
[45] Date of Patent: Nov. 4, 1997

[54] MUTANT AOX2 PROMOTER, VECTOR CARRYING SAME, TRANSFORMANT, AND PRODUCTION OF HETERLOGOUS PROTEIN

[75] Inventors: Hideyuki Ohi; Masami Miura; Shusei Uno; Masako Chuganji; Ryuji Hiramatsu; Takao Ohmura, all of Hirakata, Japan

[73] Assignee: The Green Cross Corporation, Osaka, Japan

[21] Appl. No.: 471,206

[22] Filed: Jun. 6, 1995

Related U.S. Application Data

[63] Continuation of Ser. No. 143,158, Oct. 29, 1993, abandoned.

[30] Foreign Application Priority Data

Oct. 30, 1992 [JP] Japan .................................. 4-293315
Aug. 6, 1993 [JP] Japan .................................. 5-215306

[51] Int. Cl.⁶ .......................... C12P 21/00; C12N 15/64; C12N 15/81; C07H 21/04
[52] U.S. Cl. ................ 435/69.1; 435/172.3; 435/254.23; 435/320.1; 536/24.1
[58] Field of Search .............................. 435/69.1, 172.3, 435/320.1, 254.23; 536/24.1

[56] References Cited

FOREIGN PATENT DOCUMENTS 0506040  9/1992  European Pat. Off. ........ C12N 15/81

*Primary Examiner*—Mindy Fleisher
*Assistant Examiner*—Nancy J. Degen
*Attorney, Agent, or Firm*—Sughrue, Mion, Zinn, Macpeak & Seas

[57] ABSTRACT

A mutant AOX2 promoter obtained by mutating a sequence of natural AOX2 promoter in a manner comprising at least one of the three mutation modes of (1) a region extending upstream from nucleotide 1187 inclusive and comprising at least nucleotides 845–960 is deleted, (2) nucleotide(s) is(are) replaced in region(s) in nucleotides 1274–1314, and (3) new oligonucleotide(s) is (are) inserted in region(s) in nucleotides 1274–1314, a vector carrying said mutant AOX2 promoter, a transformant into which said vector has been introduced, and a method for producing a heterologous protein, which comprises cultivating said transformant. The promoter of the present invention has remarkably enhanced activity as compared with natural AOX2 promoter, and is highly useful as a promoter to be carried in an expression vector allowing heterologous protein expression. In addition, the vector and the transformant of the invention can efficiently express and produce various useful heterologous proteins.

8 Claims, 21 Drawing Sheets

FIG. 2
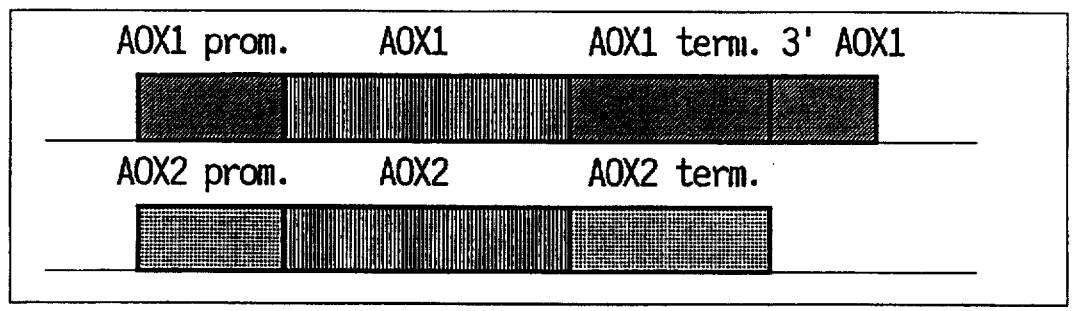
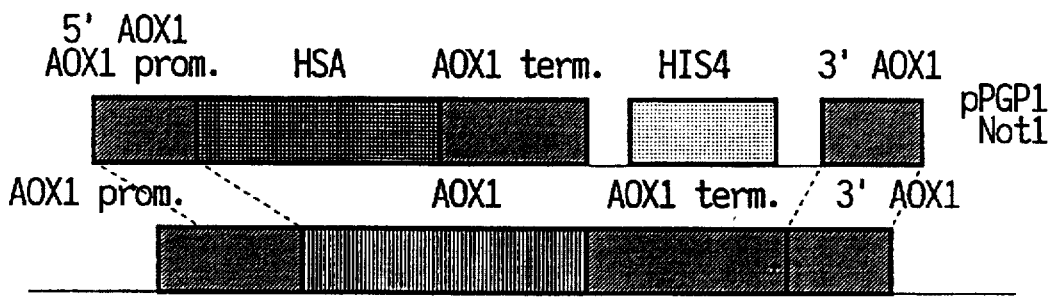
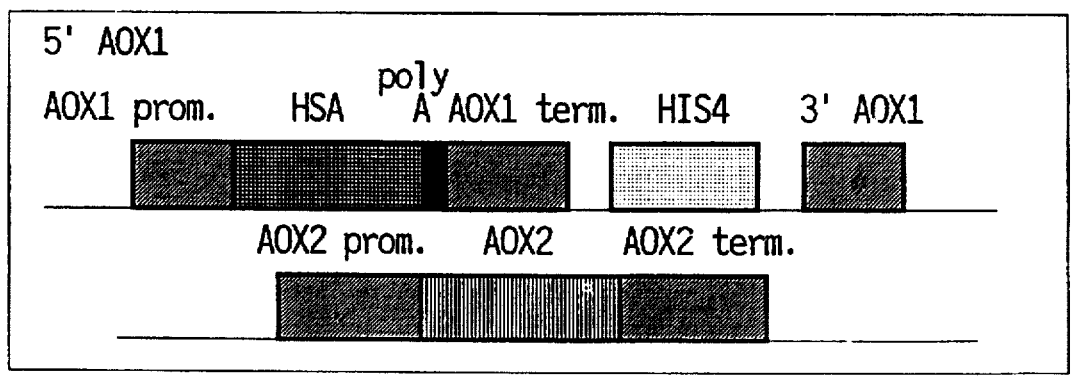

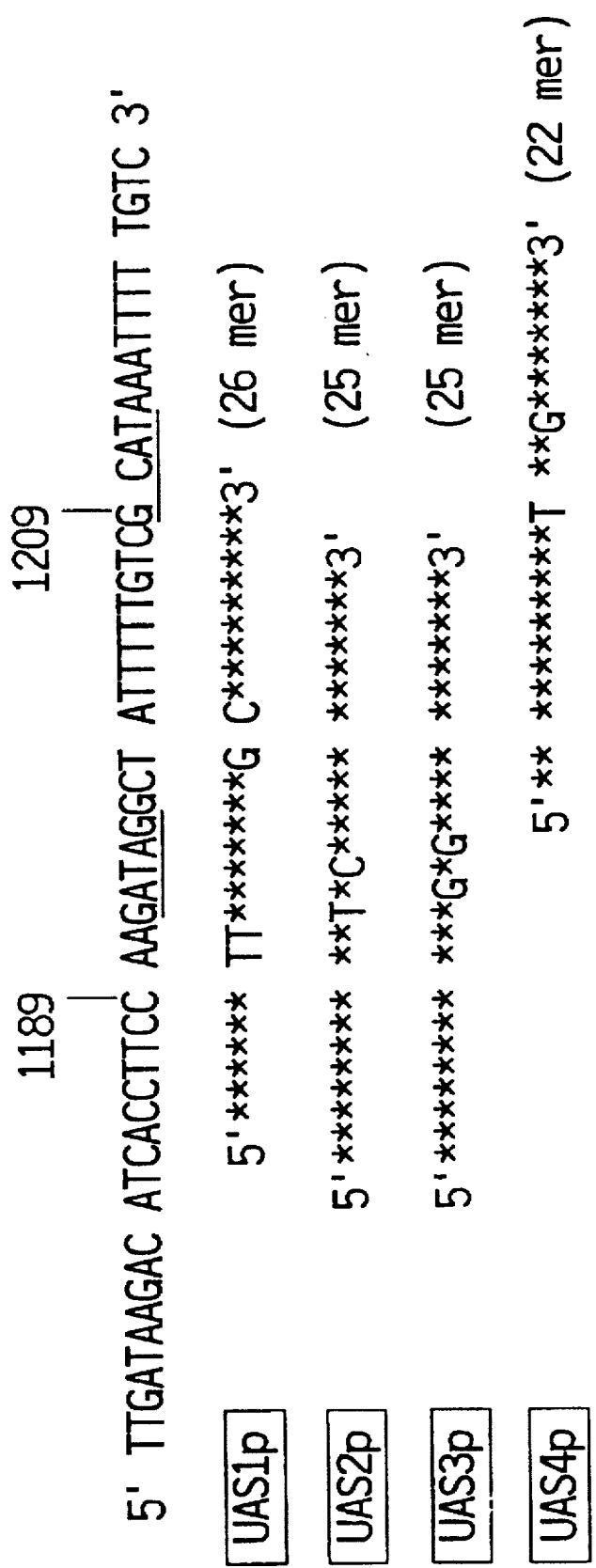

FIG. 15

```
                           1192                                    1216
                            |                                       |
P. pastoris AOX2  -341 CCAAGATAG- GCTATTTTTG -TC--GCATA AATT -312
P. pastoris AOX1  -219 TGCTGATAGC -CTAACGTTC AT---G-ATC AAAA -195
P. pastoris AOX1  -334 AAGCGATAGA GAGACTGCGC -TA-AGCATT AATG -365
                                                    (Complementary chain)
```

MUTANT AOX2 PROMOTER, VECTOR CARRYING SAME, TRANSFORMANT, AND PRODUCTION OF HETEROLOGOUS PROTEIN

This is a Continuation of application Ser. No. 08/143,158 filed 29 Oct. 1993, abandoned.

TECHNICAL FIELD OF THE INVENTION

The present invention relates to mutant AOX2 promoters preferably used for expressing heterologous protein genes, vectors carrying said promoters, transformants into which said vectors have been introduced, and methods for producing heterologous proteins, comprising culture of said transformants.

BACKGROUND OF THE INVENTION

In the field of genetic engineering, various improvements in and developments of genetic expression systems have been attempted in an effort to increase expression of genes and yield of desired proteins, and an expression system using, as a host, a methylotrophic yeast has been drawing much interest as a system for the expression of heterologous protein genes.

A methylotrophic yeast is capable of growth using methanol as a sole carbon and energy source. This mechanism is attributable to the fact that it has a gene encoding alcohol oxydase (EC1.1.3. B, hereinafter also referred to as AOX) which is an enzyme catalyzing a first reaction in the metabolism of methanol, namely, oxidation of methanol into formaldehyde.

A Pichia pastoris is one of methylotrophic yeasts, and has two kinds of AOX genes, AOX1 gene and AOX2 gene. These genes are known to respectively have a peculiar promoter at the 5' terminal non-translation region (AOX1 promoter and AOX2 promoter). The transcription activity of the AOX2 promoter is extremely poor as compared with that of the AOX1 promoter having a strong transcription activity, and alcohol oxydase actually expressed and produced are mostly derived from the AOX1 gene [Molecular and Cellular Biology, Vol. 9, 1316 (1989)].

Conventionally, an AOX1 promoter having a strong transcription activity has been used for producing a heterologous protein with a Pichia yeast. In recent years, a method for producing a heterologous protein by using a regulatory region of an AOX gene has been studied [Yeast, 5, 167–177 (1989), Japanese Patent Unexamined Publication Nos. 128790/1989 and 104290/1990, EP-A-347928], but a promoter having a stronger transcription activity for an increased expression has still been desired.

SUMMARY OF THE INVENTION

Accordingly, an object of the present invention is to provide promoters having high transcription activity, which are useful for a large-scale production of heterologous proteins, vectors carrying said promoters, and transformants into which said vectors have been introduced. Also, the present invention aims at establishing methods for producing heterologous proteins, which comprise culture of said transformants.

BRIEF DESCRIPTION OF THE DRAWINGS

FIG. 2 shows an AOX1 gene region and an AOX2 gene region of PC4130 strain wherein term. means terminator and prom. means promoter.

FIG. 12 shows nucleotide sequences of four kinds of primers to be used for introducing site-directed mutation, wherein the uppermost nucleotide sequence is the sequence of natural AOX2 promoter. Each nucleotide sequence is given following the name of the four primer UASps, and * means that the sequence is the same as that of natural AOX2 promoter (SEQ ID. NO. 26).

FIG. 15 shows nucleotides homologous between AOX2 promoter and AOX1 promoter (SEQ ID. NO. 27–29).

FIG. 18(a) shows the growth and HSA production with increasing cultivation time (~96 hours) of pYI070 transformant (70-7) and FIG. 18(b) shows the growth and HSA production with increasing cultivation time (~96 hours) of pYI071 transformant (71-7); where ■ is 70-7/D/HSA, ■ is 70-7/M/HSA, ■ is 70-7/DM/HSA, ─▲─ is 70-7/D/OD, ─●─ is 70-7/M/OD, and ─■─ is 70-7/DM/OD, by which shown is transformant/medium/object measured [D of the medium means YPD medium, M means YPM medium, and DM means YPDM medium; HSA of the object measured means HSA production, and OD means cell growth (OD 540 nm)].

DETAILED DESCRIPTION OF THE INVENTION

Figure 1:
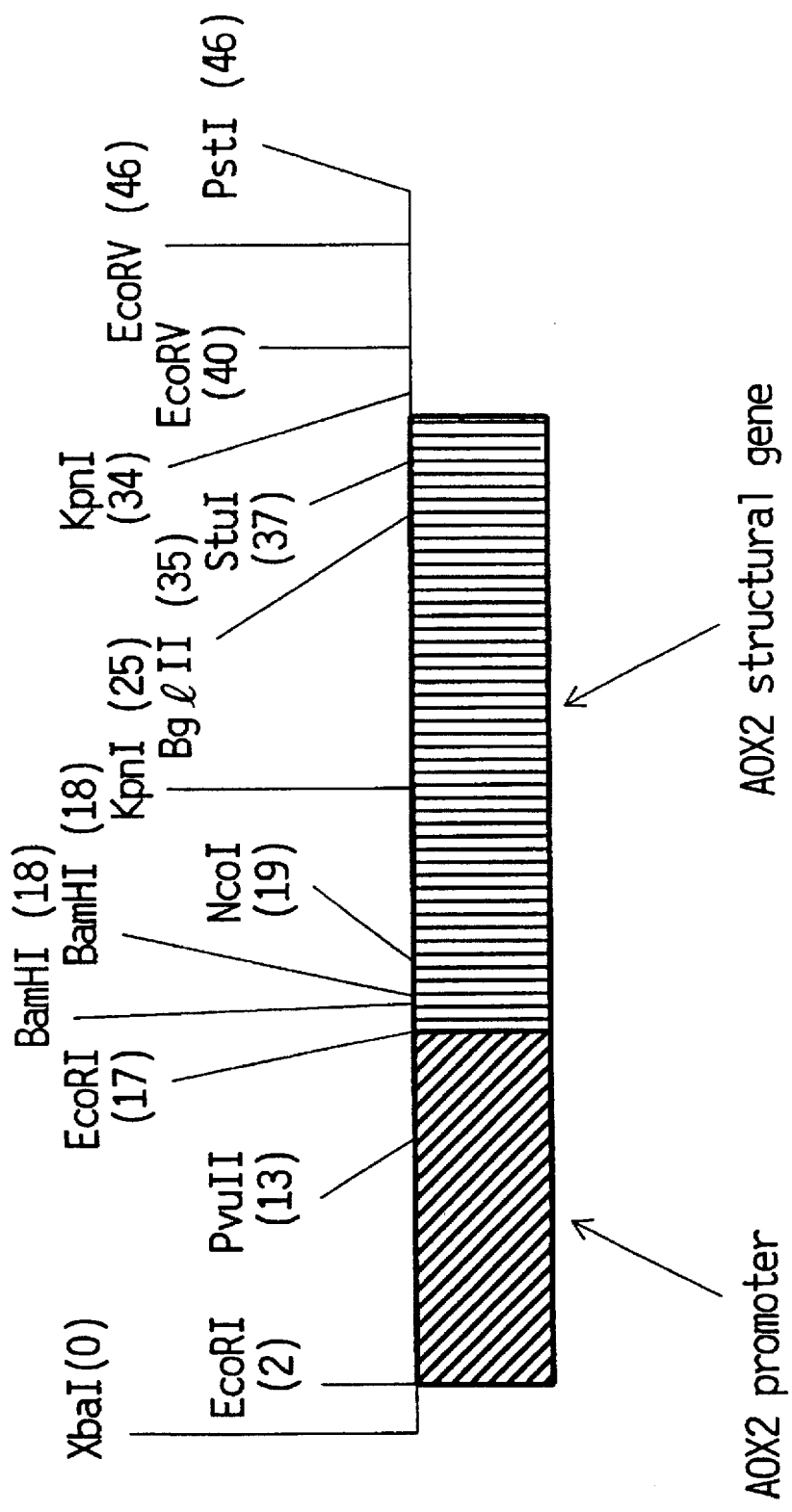
FIG. 1 shows a restriction enzyme map of the region of AOX2 gene and its vicinity, wherein the figures in parentheses indicate the distance (×100 nucleotide) when XbaI recognition site is taken as 0.

The present inventors have conducted intensive studies with the aim of developing a promoter having high transcription activity, and found that by using, as a promoter, a DNA fragment obtained by mutating a specific region in the transcription regulatory region of AOX2 gene, a heterologous protein gene located downstream from the specific region can be efficiently expressed, and completed the invention.

Accordingly, the present invention relates to a mutant AOX2 promoter obtained by mutating a nucleotide sequence of natural AOX2 promoter (SEQ ID. NO. 1) in a manner comprising at least one of the three mutation modes noted below.

(1) A region extending upstream from nucleotide 1187 inclusive and comprising at least nucleotides 845–960 is deleted.

(2) Nucleotide(s) is(are) replaced in region(s) in nucleotides 1274–1314.

(3) New oligonucleotide(s) is(are) inserted in region(s) in nucleotides 1274–1314.

Also, the present invention relates to a vector carrying said mutant AOX2 promoter, a transformant into which said vector has been introduced, and a method for producing a heterologous protein, which comprises cultivating said transformant.

The mutant AOX2 promoter of the invention may comprise either one of or a combination of the above-mentioned mutation modes (1)–(3). The following mutation modes are exemplified.

In the description to follow, nucleotide numbers are those of the nucleotide sequence of natural AOX2 promoter (SEQ. ID NO. 1), unless otherwise specified.

(1) A mutant AOX2 promoter wherein, in the nucleotide sequence of natural AOX2 promoter (SEQ ID. NO. 1), a region extending upstream (5' terminal) from nucleotide 1187 inclusive and comprising at least nucleotides 845–960 has been deleted.

The deletion site is not subject to any particular limitation insofar as it is a region extending upstream from nucleotide 1187 and it comprises at least nucleotides 845–960. As long as the deletion takes place in the thus-specified region, the number of the deleted nucleotide may be any, and the number of the deletion site may be one to several. Examples thereof include a mutant AOX2 promoter obtained by deleting 489 nucleotides 749–1187 from the nucleotide sequence of natural AOX2 promoter (SEQ. ID NO. 2), a mutant AOX2 promoter obtained by deleting all nucleotides extending upstream from nucleotide 960 inclusive (SEQ.ID.NO.3), a mutant AOX2 promoter obtained by deleting all nucleotides extending upstream from nucleotide 1187 inclusive (SEQ.ID.NO.4).

(2) A mutant AOX2 promoter wherein, in the nucleotide sequence of natural AOX2 promoter, nucleotide(s) is(are) replaced in region(s) in nucleotides 1274–1314.

The replacing site is not subject to any particular limitation insofar as it is between nucleotides 1274 and 1314. The number of the replaced nucleotide may be one or more, and the replacing site may be one to several.

Preferably, thymine (1274, T) is replaced with cytosine (C) (SEQ.ID.NO.5).

(3) A mutant AOX2 promoter wherein, in the nucleotide sequence of natural AOX2 promoter, a region extending upstream from nucleotide 1187 inclusive and comprising at least nucleotides 845–960 has been deleted, and nucleotide(s) is(are) replaced in region(s) in nucleotides 1274–1314.

This type of mutant AOX2 promoter comprises the above-mentioned mutation modes (1) and (2), and is not subject to any particular limitation insofar as it satisfies the above-mentioned requirements for (1) and (2).

Specifically, a DNA fragment obtained by replacing T (1274) with C and completely deleting a region extending upstream from nucleotide 1187 inclusive from the sequence of natural AOX2 promoter (SEQ.ID.NO.6) is exemplified.

(4) A mutant AOX2 promoter wherein, in the nucleotide sequence of natural AOX2 promoter, new nucleotide(s) has(have) been added in region(s) in nucleotides 1274–1314.

The addition site is not subject to any particular limitation insofar as it is between nucleotides 1274 and 1314. The number of the nucleotide to be added in said sequence may be any, and the addition site may be one to several.

Specifically, a mutant AOX2 promoter obtained by inserting a 19 bp oligonucleotide corresponding to nucleotides 1296–1314 (SEQ.ID.NO.7) in between nucleotide 1295 and nucleotide 1296 is exemplified (SEQ.ID.NO.8).

(5) A mutant AOX2 promoter wherein, in the nucleotide sequence of natural AOX2 promoter, a region extending upstream from nucleotide 1187 inclusive and comprising at least nucleotides 845–960 has been deleted, and new oligonucleotide(s) has(have) been added in region(s) between nucleotides 1274 and 1314.

This type of mutant AOX2 promoter comprises the above-mentioned mutation modes (1) and (4), and is not subject to any particular limitation insofar as it satisfies the above-mentioned requirements for (1) and (4).

Specifically, a mutant AOX2 promoter obtained by inserting an oligonucleotide of (SEQ.ID.NO.7) in between nucleotide 1295 and nucleotide 1296, and completely deleting a region extending upstream from nucleotide 1187 inclusive is exemplified (SEQ.ID.NO.9).

Note that the nucleotide sequences (SEQ ID. NOS. 2, 3, 4, 5, 6, 8, and 9) depicted in the Sequence List to be given below are only for illustrating purpose, and the mutant AOX2 promoter of the invention is not limited to them.

In addition, the mutant AOX2 promoter of the present invention is required to have a nucleotide sequence as shown in (SEQ.ID.NO.10) in the Sequence List (Upstream Activation Sequence, hereinafter referred to as UAS).

The mutant AOX2 promoter, a vector carrying said promoter, and a transformant into which said vector has been introduced are prepared, for example, as follows.

(I) Mutant AOX2 promoter

The mutant AOX2 promoter of the present invention is prepared by treating a natural AOX2 promoter by genetic engineering. Specifically, a particular site of the natural AOX2 promoter nucleotide sequence is deleted, replaced, or added with new nucleotides. These steps may be performed using conventional genetic engineering techniques, and usable methods are, for example, site-directed deletion [Nucl. Acids Res., 11, 1645 (1983)], site-directed mutagenesis, restriction enzyme treatment, a method utilizing synthetic gene, and PCR method.

Alternatively, it can be prepared by chemical synthesis based on the nucleotide sequence of the mutant AOX2 promoter of the invention.

Also, the mutant AOX2 promoter of the present invention may be prepared from a strain with poor methanol utilization due to the fact that AOX1 gene has been genetically deteriorated and usable is only AOX2 gene. That is, a strain with poor methanol utilization is subcultured in a medium containing methanol as a sole carbon source to cause mutation into a strain with improved methanol utilization (Super High Grade Strain; SHG strain), from which the AOX2 promoter of the invention can be prepared.

(II) (i) Construction of recombinant vector

The thus-obtained mutant AOX2 promoter is inserted into a suitable plasmid vector or a phage vector and used as a vector for expressing a heterologous protein.

The insertion of said promoter into various plasmids and phages can be done according to a conventional method for DNA recombination such as a method described in Molecular Cloning (Cold Spring Harbor Lab., 1989).

(ii) Construction of recombinant expression vector

The recombinant expression vector of the present invention with which a heterologous protein gene is expressed under the control of the mutant AOX2 promoter, can be constructed by inserting a gene of the desired heterologous protein into a 3'-flanking region of the mutant AOX2 promoter in the recombinant vector obtained as above, via a translation initiation codon.

Alternatively, it may be constructed by cleaving out the mutant AOX2 promoter of the present invention from the above-mentioned recombinant plasmid vector or phage vector by using a restriction enzyme, and replacing a promoter region of a vector having a structural gene for a heterologous protein with the mutant AOX2 promoter by using a restriction enzyme, DNA ligase, etc.

More specifically, the vector of the present invention is constructed in such a manner that (1) mutant AOX2 promoter, (2) ribosome binding site, (3) translation initiation codon, (4) DNA having nucleotide sequence encoding signal peptide, (5) DNA having nucleotide sequence encoding heterologous protein, (6) translation termination codon, (7) terminator, (8) selection marker gene, (9) autonomously replicating sequence, and (10) homologous region are sequentially comprised as necessary in the direction to the downstream, for the efficient expression of a heterologous protein.

There is imposed no particular limitation on the structural gene so long as it encodes the desired heterologous protein such as human serum albumin, prourokinase, tissue plasminogen activator, hepatitis B surface antigen, and various interferons, and it may be prepared by any method. Particularly, cDNA synthesized from mRNA, genomic DNA, chemically-synthesized DNA and DNA constructed by combining these are examplified.

Specific examples include HSA structural gene, AOX1 structural gene and AOX2 structural gene.

The above-mentioned structural gene may have ATG as a translation initiation codon at the 5' terminal of the gene, and it may have a translation termination codon at the 3' terminal of the gene. Examples of the translation termination codon include TAA, TGA, and TAG. One or more of these codons may be combinedly incorporated in each region, and are subject to no limitation.

There is no particular limitation imposed on the terminator insofar as it suits a host to be used for the expression of a nucleotide sequence encoding the desired heterologous protein. For example, AOX1 terminator or AOX2 terminator may be used.

Examples of the selection marker gene are antibiotic-resistant gene and auxotrophic gene. In general terms, when the host is a bacterium, an antibiotic-resistant gene may be used, and examples thereof include cycloheximide-resistant gene, ampicillin-resistant gene, chloramphenicol-resistant gene, bleomycin-resistant gene, hygromycin-resistant gene, and G-418 resistant gene. When the host is other than bacteria, such as a yeast, an auxotrophic gene may be used, and examples thereof include HIS4, URA3, LEU2, and ARG4. These selection markers are preferably incorporated solely or in combination into suitable sites in said vector.

Specific examples of the homologous locus to be integrated into the host chromosome are HIS4, URA3, LEU2, ARG4, and TRP1.

The vector of the present invention may comprise several mutant AOX2 promoters of the invention which are linked (i.e. tandem dimer, tandem trimer). In this case, it is preferable that translation initiation codon be not interposed between the promoters.

(III) transformant and its culture

The transformant of the present invention is prepared by introducing the recombinant expression vector as obtained above into a suitable host cell.

More detailedly, the transformant of the present invention is prepared by introducing the recombinant expression vector of (II) above into a host by a known method such as competent cell method (J. Mol. Biol., 53, 154, 1970), protoplast polyethylene fusion method (Proc. Nat. Acad. Sci. USA, 75, 1929, 1978), calcium phosphate method (Science, 221, 551, 1983), DEAE dextran method (Science, 215, 166, 1982), Electric pulse method (Proc. Natl. Acad. Sci. USA, 81, 7161, 1984), in vitro packaging method (Proc. Natl. Acad. Sci. USA, 72, 581, 1975), virus vector method (Cell, 37, 1053, 1984), or microinjection method (Exp. Cell. Res., 153, 347, 1984).

As the host to be used, a microorganism such as *Echerichia coli*, *Bacillus subtilis*, or yeast is exemplified, with preference given to a yeast, specifically Pichia yeast, GTS115 (NRRL deposit number Y-15851).

The vector introduced in a host cell may be integrated into a chromosome by insertion or replacement. Or, it may be present as a plasmid.

The number of copies of an exogenous gene to be introduced into a host may be single or plural.

The transformant thus obtained is cultivated in a suitable, known medium selected according to the host to be used for the production of the desired recombinant heterologous protein. The medium contains carbon source, nitrogen source, minerals, vitamins, and drugs essential for the growth of said transformant.

Examples of the medium include LB medium (manufactured by Nissui Seiyaku, Japan) and M9 medium (J. Exp. Mol. Genet., Cold Spring Harbor Laboratory, New York, p. 431, 1972) when the host is *Echerichia coli*; and YPD medium (1% bacto yeast extract, 2% bacto peptone, 2% glucose), YPG medium (1% bacto yeast extract, 2% bacto peptone, 2% glycerol), YPM medium (1% bacto yeast extract, 2% bacto peptone, 2% methanol), YPDM medium (1% bacto yeast extract, 2% bacto peptone, 2% dextrose, 2% methanol), YNB liquid medium containing 0.1–5% methanol (0.7% yeast nitrogen base, manufactured by Difco), YP medium containing 0.01–5% methanol (1% bacto yeast extract, manufactured by Difco, 2% Poly Peptone (manufactured by Daigo Elyosha, Japan), and SMM medium (2% methanol, 0.5% $CH_3COONH_4$ synthetic medium) when the host is a yeast.

Cultivation is usually carried out at a temperature between 15° C. and 45°C., preferably about 30° C. for 20–360 hours, and aeration and/or agitation may be applied where necessary. The pH of the culture is preferably from 5 to 8.

After culture, the desired heterologous protein accumulated in the culture supernatant or transformant is extracted and purified by known methods. For example, salting-out, solvent precipitation, dialysis, ultrafiltration, gel electrophoresis, gel filtration chromatography, ion exchange chromatography, reverse phase chromatography, affinity chromatography, and so on may be used in combination.

Note that various techniques, reactions, and analysis methods to be used in the present invention are known to those of ordinary skill in the art. Also, enzymes, plasmids, hosts, and the like are commercially available.

The present invention is hereinbelow more detailedly described by way of examples and experimental examples, to which the invention is not limited.

All the enzymes used in the following examples and experimental examples were obtained from commercial supply sources such as Takara Shuzo Kabushiki Kaisha, Japan, unless specifically identified.

Buffers for enzyme reactions and reaction conditions followed manufacturer's recommendations for each enzyme unless particularly specified.

*Pichia pastoris* GTS115, PC4130, PC4105, and plasmid pPGP1 were obtained from Phillips Petroleum.

Transformation of *Echerichia coli* using a plasmid as a vector, plaque hybridization, and electrophoresis were conducted according to the method described in Molecular Cloning, Cold Spring Harbor Laboratory (1982).

EXAMPLE 1

Cloning of AOX2 gene, and preparation of recombinant vector

The sequence of and a restriction enzyme map of AOX2 gene and its vicinity have been reported by Cregg et al., Mol. Cell. Biol., 9, 1316–1323 (1989) and Koutz et al., YEAST, 5, 167–177 (1989). Referring to the reports, cloning of AOX2 gene was designed. The restriction enzyme map of AOX2 gene and its vicinity is shown in FIG. 1.

First, a chromosome DNA was extracted from PC4130 strain and purified according to the method of Cameron et al. [Nucleic Acids Res., 4, 1429 (1977)].

The PC4130 strain comprises a gene region which was obtained by replacing a part of the AOX1 gene region of GTS115 (HIS4) with a NotI-fragment of pPGP1 plasmid (a plasmid having a transcription unit to permit HSA expression under the control of AOX1 promoter) (FIG. 2).

This chromosome DNA was completely digested with restriction enzymes XbaI and PstI in such a manner that AOX2 promoter region, AOX2 structural gene, and AOX2 terminator region are completely included therein.

The DNA fragment thus obtained was precipitated with ethanol, centrifuged, dried, and dissolved in sterile water. Then, EcoRI methylase (manufactured by Takara Shuzo Kabushiki Kaisha, Japan) was added thereto and allowed to react. Thereafter, TE saturated phenol.chloroform extraction, and chloroform extraction were sequentially conducted. The water layer was subjected to ethanol precipitation, centrifuged, dried, and dissolved in sterile water. Using a DNA blunting kit (manufactured by Takara Shuzo Kabushiki Kaisha, Japan), DNA fragment ends were blunted, and ligated with EcoRI linker d(pG-G-A-A-T-T-C-C) (manufactured by Takara Shuzo Kabushiki Kaisha, Japan) using a DNA ligation kit (manufactured by Takara Shuzo Kabushiki Kaisha, Japan). Ethanol precipitation was again conducted. After centrifugation and drying, the precipitate was dissolved in sterile water, to which was added EcoRI, and incubation was done at 37° for 1 hour. The mixture was subjected to 1% agarose gel electrophoresis; the band corresponding to 4–5 kb was cut out from the agarose gel; and DNA was recovered from the gel by elution and purification using GENE CLEAN II (manufactured by BIO 101). The obtained DNA was dissolved in sterile water.

The purified DNA fragment was ligated with I λgt10 arms (Protoclone™ System, manufactured by Promega), and subjected to in vitro packaging using Gigapack-GOLD3 (manufactured by Stratagene).

The recombinant phage was infected to *E. coli* C600hf1 strain which had been adjusted to $A_{600}$=2, and inoculated on an NZY plate (1% NZ amine, 0.5% sodium chloride, 0.5% yeast extract, 0.02% magnesium sulfate, 1.5% agar powder) such that about 500 plaques were grown on each plate. From the plaques grown, clones containing the above-mentioned DNA fragment (positive clone) were selected and obtained by colony hybridization method. That is, using four nylon membranes Colony/Plaque Screen™ (manufactured by NEN), the plaques were transferred to the membranes, followed by denaturation, neutralization, and immobilization. Used as a probe was a fragment obtained by digesting, with EcoRV and BalII, the former half of an AOX1 structural gene derived from *Pichia pastoris* IFO 1013 strain, and then labelling the gene with $^{32}P$ using a random primer labelling kit (manufactured by Takara Shuzo Kabushiki Kaisha). Prehybridization was conducted in a solution of 1% BSA, 1 mM EDTA, 0.5M $NaH_2PO_4$ (pH 7.2), and 7% SDS at 65° C. for 5 minutes. Hybridization was conducted in a solution of 1% BSA, 1 mM EDTA, 0.5M $NaH_2PO_4$ (pH 7.2), 7% SDS, and $^{32}P$-probe at 65° C. overnight, which was followed by incubation/washing in a solution of 0.5M $NaH_2PO_4$ (pH 7.2) at room temperature for 10 minutes, and further incubation (3 times) In a solution of 0.5% BSA, 1 mM EDTA, 40 mM $NaH_2PO_4$ (pH 7.2), and 5% SDS at 37° C. for 30 minutes. The filter was air-dried, and left layered on an X-ray film in an X-ray film exposure cassette at −80° C. for 16 hours for autoradiography. As a result, 2 positive clones were obtained. One of them was cultivated to allow growth of phages to extract phage DNA. The DNA was cleaved with EcoRI, and subjected to agarose electrophoresis to confirm presence of the desired fragments (1.5 kb and 2.9 kb).

Figure 3:
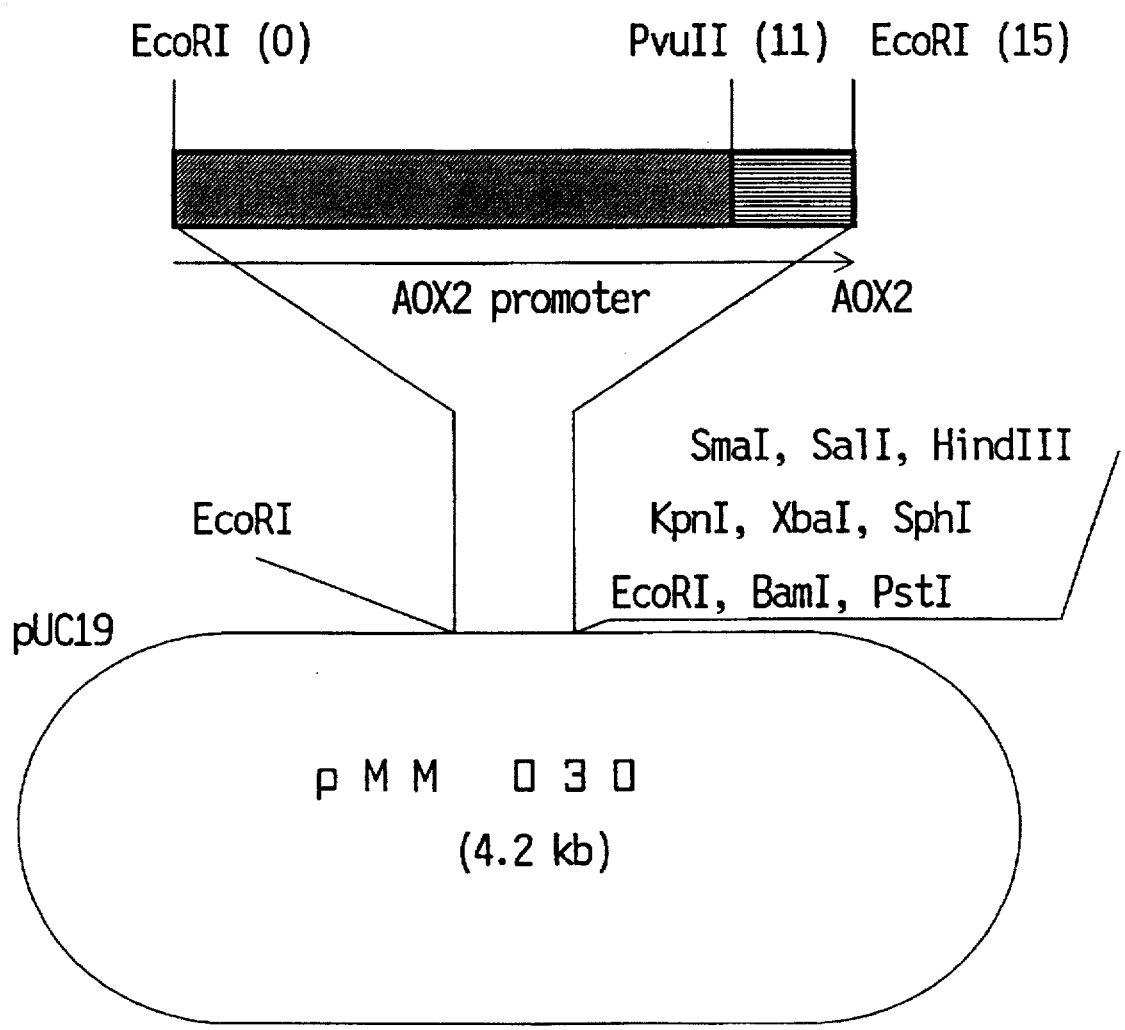
FIG. 3 shows a restriction enzyme map of the AOX2 promoter cloned in pMM030 plasmid, where the figures in parentheses indicate the distance (×100 nucleotide) when EcoRI recognition site is taken as 0.
Figure 4:
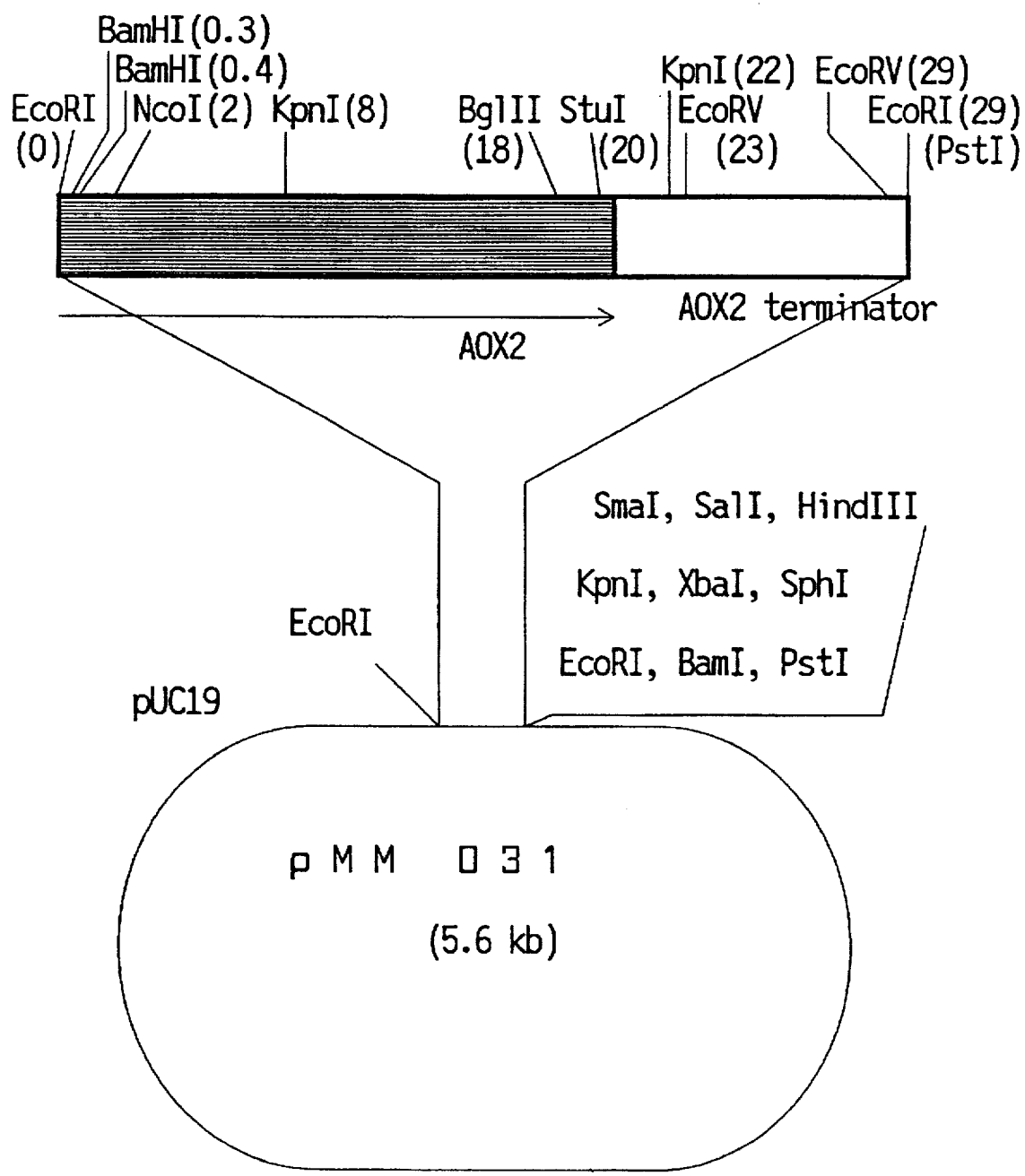
FIG. 4 shows a restriction enzyme map of the AOX2 structural gene cloned in pMN031 plasmid, where the figures in parentheses indicate the distance (×100 nucleotide) when EcoRI recognition site is taken as 0.

On the other hand, plasmid pUC19 (manufacture by Bethesda Research Laboratories) having an ampicillin-resistant gene as a selection marker was cleaved with EcoRI, treated with alkali phosphatase, and recovered. The DNA fragment obtained from the above-mentioned phage and digested with EcoRI was ligated with the EcoRI-cleaved plasmid to construct a plasmid vector, which was then introduced into *E. coli* HB101 to give a transformant. The transformant was inoculated on an L plate containing 40 μg/ml ampicillin and cultured at 37° C. overnight. [The L plate was prepared as follows. Tris base 0.62 g, polypeptone 10 g, yeast extract 5 g, and sodium chloride 5 g were dissolved in water to make the total amount 1 l, and thereto was added 15 g of agar powder, followed by autoclave. After cooling, ampicillin was added, and the mixture was dispensed to a plastic Schale and immobilized to give a plate.] The colonies were screened (EcoRI-digested fragment was confirmed by miniprep) and it was confirmed that clones carrying pUC19 containing 1.5 kb fragment and 2.7 kb fragment were obtained. The clones were subjected to shake culture at 37° C. overnight In a 40 µg/ml ampicillin-containing super broth (a culture medium obtained by mixing A solution and B solution; A solution being prepared by dissolving bactotryptone 12 g, yeast extract 24 g, and glycerol 5 ml in water to make the total amount 900 ml, followed by autoclave, and B solution being prepared by dissolving potassium dihydrogenphosphate 3.81 g, and dipotassium hydrogenphosphate 12.5 g in water to make the total amount 100 ml, followed by autoclave) in a ratio of 9:1 (v/v), and the plasmid DNA was extracted and purified in a large amount by alkali-SDS method. The plasmid comprising the AOX2 promoter region was named pMM030 (FIG. 3) and the plasmid comprising the AOX2 structural gene and terminator was named pMM031 (FIG. 4). The size of the fragments produced by the digestion of these plasmids with various restriction enzymes showed the same pattern as had been reported.

EXAMPLE 2

Determination of nucleotide sequence of AOX2 promoter region

The plasmid vector pMM030 obtained in Example 1 was digested with EcoRI. The obtained 1.5 kb fragment was recovered, and the DNA fragment was treated with a DNA blunting kit (manufactured by Takara Shuzo Kabushiki Kaisha) to give a DNA fragment having blunt ends.

On the other hand, plasmid pUC19 was digested with XbaI, treated with Mung Bean Nuclease (manufactured by Takara Shuzo Kabushiki Kaisha), and treated with alkali phosphatase, followed by ligation of the DNA fragment obtained above with the XbaI cleavage site. By these procedures, plasmids wherein AOX2 promoter region DNA was subcloned to the XbaI site of pUC19 were obtained.

These plasmids were treated using a deletion kit for Kilo-Sequence (manufactured by Takara Shuzo Kabushiki Kaisha) to prepare 5 or 6 clones of deletion mutants having an insertion size varying by 150 to 300 bp. The nucleotide sequence of these deletion mutants was identified using M13 dideoxy sequencing kit (manufactured by Takara Shuzo Kabushiki Kaisha). As a result, the entire nucleotide sequence for 1.5 kb upstream from ATG of the AOX2 structural gene was identified.

EXAMPLE 3

Figure 5:
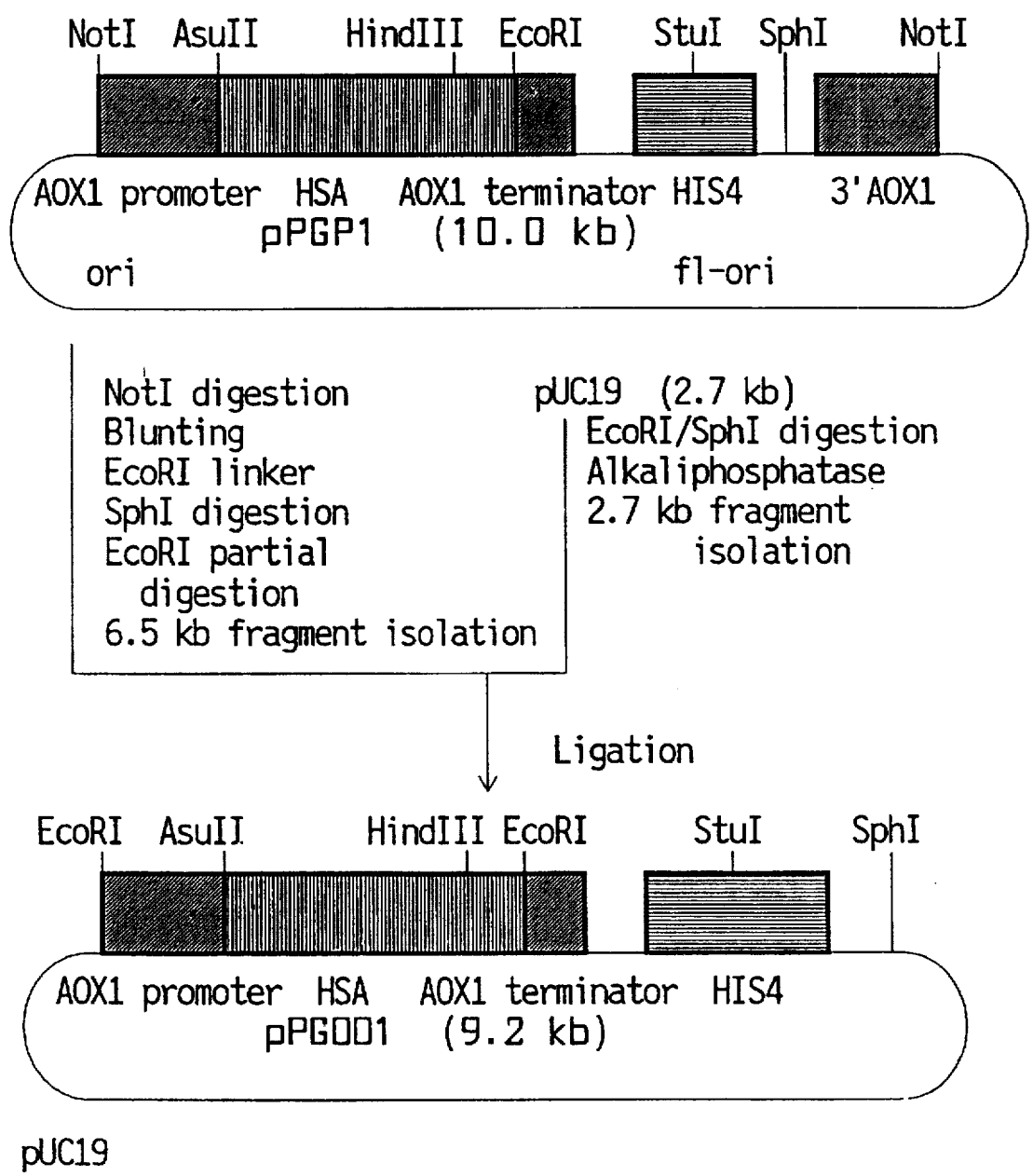
FIG. 5 depicts the construction of pPG001.
Figure 6:
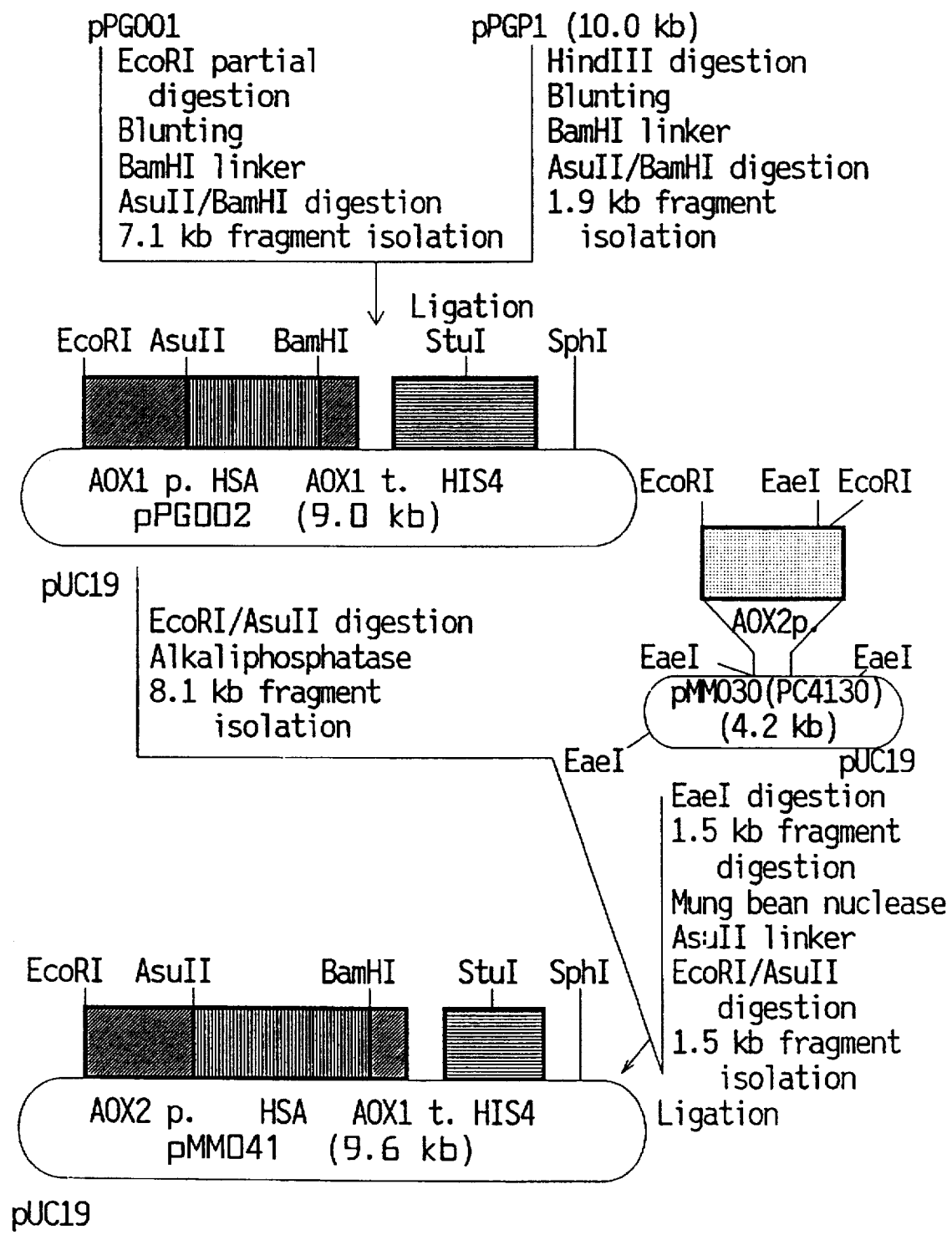
FIG. 6 depicts the construction of pMN041 where HSA is expressed under the control of AOX2 promoter. In the Figure, t. means terminator and p. means promoter.
Figure 7:
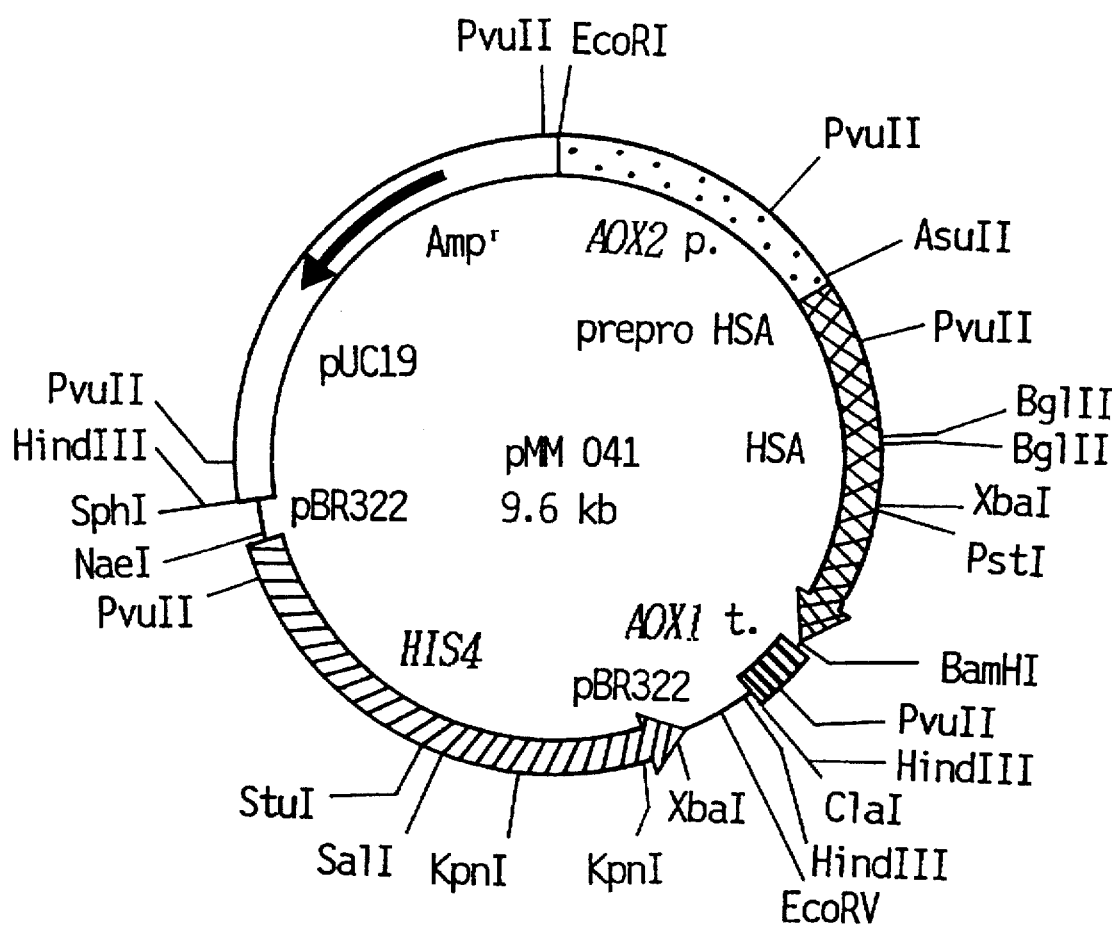
FIG. 7 shows a restriction enzyme map of an HSA expression vector pMN041, wherein AOX2 p. is AOX2 promoter, AOX1 t. is AOX1 terminator, prepro HSA is a prepro HSA sequence, HSA is HSA cDNA, HIS4 is *P. pastoris* HIS4 gene, Amp$^r$ is an ampicillin-resistant gene, pUC19 is a pUC19-derived sequence, and pBR322 is a pBR322-derived sequence.

Construction of HSA expression vector controlled by AOX2 promoter pPGP1 was digested with NotI, and blunted using a DNA blunting kit (manufactured by Takara Shuzo Kabushiki Kaisha). Thereto was ligated EcoRI linker d(pG-G-A-A-T-T-C-C) (manufactured by Takara Shuzo Kabushiki Kaisha). A complete digestion with SphI and partial digestion with EcoRI were conducted, and 6.5 kb DNA fragment was recovered and purified. pUC19 was digested with EcoRI and SphI, subjected to alkali phosphatase treatment, and ligated with the above-mentioned fragment. Thus, a pUC19-derived plasmid pPG001 having HIS4 as a selection marker wherein HSA was expressed under the control of AOX1 promoter was obtained (FIG. 5). pPG001 was partially digested with EcoRI and blunted with a DNA blunting kit (manufactured by Takara Shuzo Kabushiki Kaisha). On the other hand, a BamHI linker having a sequence of GGGATCCC was synthesized by phosphoamidite method using a DNA synthesizer Model 381A (manufactured by Applied Biosystem), which was then phosphorylated with T4 polynucleotide kinase (manufactured by Takara Shuzo Kabushiki Kaisha) and ligated with the fragment of pPG001 previously blunted as described. Then, it was digested with AsuII and BamHI, and a 7.1 kb fragment was purified. Meanwhile, pPGP1 was digested with HindIII, and blunted using a DNA blunting kit (manufactured by Takara Shuzo Kabushiki Kaisha), therewith ligated was BamHI linker d(pG-G-G-A-T-C-C-C) (manufactured by Takara Shuzo Kabushiki Kaisha). It was digested with AsuII and BamHI, and a 1.9 kb fragment was purified, with which the above-mentioned 7.1 kb fragment was ligated to give pPG002 (FIG. 6).

pMM030 was digested with EaeI and a 1.5 kb fragment was recovered. It was blunted by Mung Bean Nuclease treatment (manufactured by Takara Shuzo Kabushiki Kaisha). Then, using a DNA synthesizer Model 381A (manufactured by Applied Biosystem), AsuII linker having a sequence of CTTCGAAG was synthesized by phosphoamidite method. The AsuII linker was phosphorylated with T4 polynucleotide kinase (manufactured by Takara Shuzo Kabushiki Kaisha) and ligated with the fragment of pMM030 previously blunted as described. Then, it was digested with EcoRI and AsuII, and a 1.5 kb AOX2 promoter fragment was recovered. Meanwhile, plasmid pPG002 having an HIS4 region wherein HSA expressed under the control of AOX1 promoter was digested with EcoRI and AsuII, and an 8.1 kb fragment lacking AOX1 promoter region was treated with alkali phosphatase and recovered, after which it was ligated with the AOX2 promoter region 1.5 kb fragment to prepare a plasmid pMM041 which allows expression of HSA under the control of AOX2 promoter (FIG. 6). The restriction enzyme map of pMM041 is shown in FIG. 7.

EXAMPLE 4

Amplification of AOX2 promoter gene which has undergone deletion of 5' upstream region, by PCR method In order to amplify by PCR method, using AOX2 promoter fragments having a length of an upstream region from the translation initiation codon ATG, of 803 bp, 684 bp, 568 bp, 462 bp, 341 bp, 273 bp, 248 bp, or 214 bp, the primer sequence with an EcoRI site at the 5' terminal or an AsuII site at the 3' terminal was designed, synthesized using a 392 type DNA/RNA synthesizer (manufactured by Applied Biosystem) by phosphoamidite method, and purified by an NAP 10 column (manufactured by Pharmacia). The respective sequences are given in Table 1 (SEQ. ID. NOS. 11–19).

TABLE 1

| Primer | Primer sequence nucleotide sequence | plus strand or reverse strand |
|---|---|---|
| PCR60 | 5'-GAATTCACTAAGCGACTCATCATC-3' | plus |
| PCR63 | 5'-GAATTCTCCGGAACTGATCCGACT-3' | plus |
| PCR64 | 5'-GAATTCTCATTGGACTCTGATGAG-3' | plus |
| PCR65 | 5'-GAATTCCAGCTGTCAGCTACCTAG-3' | plus |
| PCR71 | 5'-GAATTCCCAAGTAGGCTATTTTTG-3' | plus |
| PCR66 | 5'-GAATTCTACAGAAGCGTCCTACCC-3' | plus |
| PCR67 | 5'-GAATTCGTTGAGATCCGGAGAAAA-3' | plus |
| PCR68 | 5'-GAATTCCGATTATTGGTATAAAAG-3' | plus |
| PCRRV | 5'-TTCGAAGTTTTTCTCAGTTGATTT-3' | reverse |

Using any of the plus strands and the reverse strand primer PCRRV, PCR was performed with *Pichia pastoris* chromosome DNA. The PCR apparatus was Perkinelmer DNA thermalcycler (manufactured by CETUS CORPORATION) and the reagent was Gene Amp™ DNA amplification kit (manufactured by Takara Shuzo Kabushiki Kaisha). Low molecule substances present in a reaction mixture were removed by Ultrafree C3TK (manufactured by Millipore), and the resulting mixture was used as a purified PCR product.

EXAMPLE 5

Construction of HSA expression vector controlled by 5'-deleted AOX2 promoter

Figure 8:
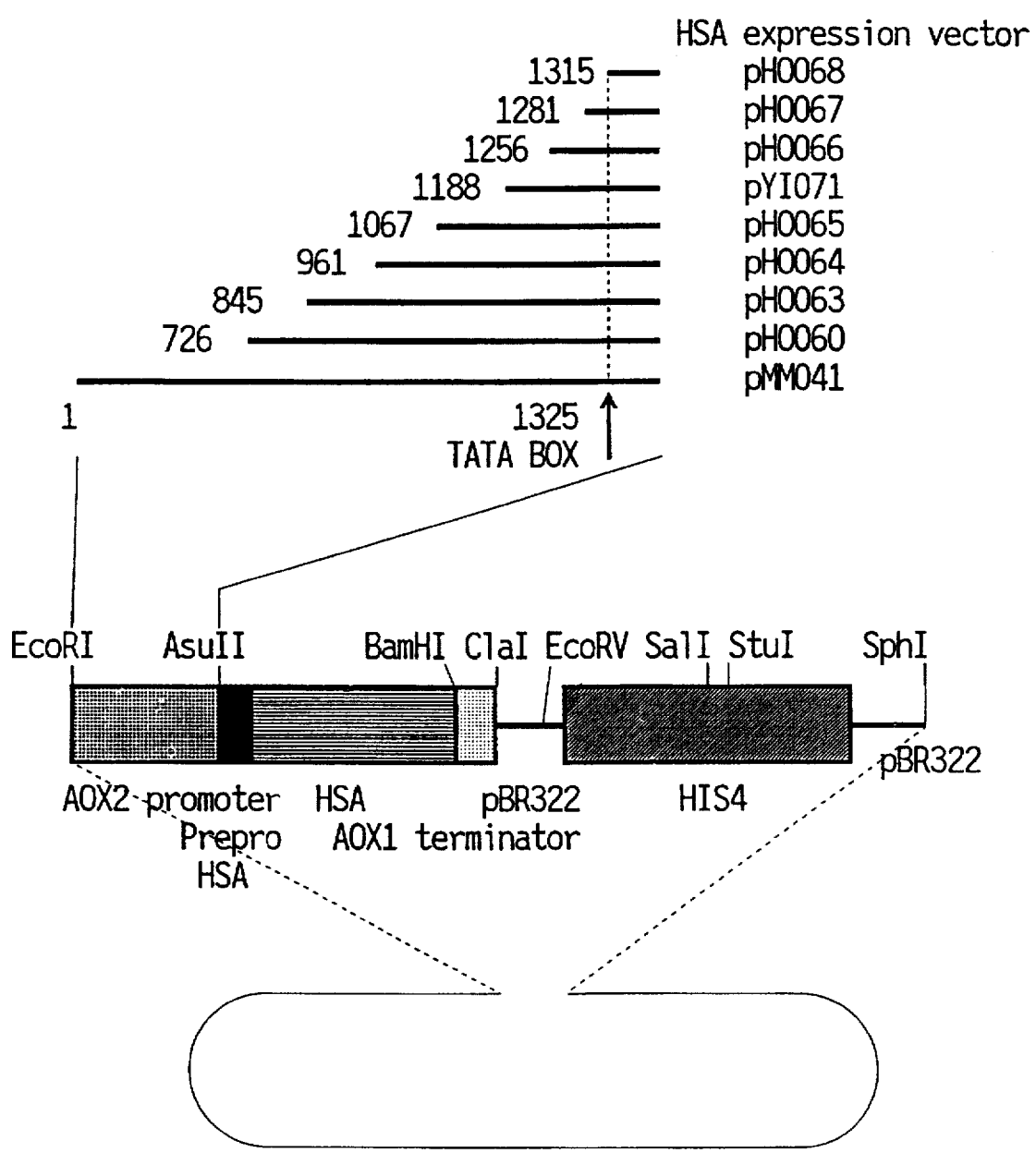
FIG. 8 shows an HSA expression vector controlled by an upstream-deleted AOX2 promoter.

An HSA expression vector pMM041 was double-digested with EcoRI and AsuII; natural AOX2 promoter was separated and removed by agarose gel electrophoresis; and the purified PCR product which was double-digested with EcoRI and AsuII, as obtained in Example 4 was inserted in the vector portion, whereby to produce a plasmid containing a 5'-deleted AOX2 promoter. So as to confirm that the inserted DNA fragment was an AOX2 promoter gene which underwent deletion of 5'-upstream region, the nucleotide sequence was determined by dideoxy method using a fluorescence primer by ALF DNA sequencer (manufactured by Pharmacia). The fluorescence primer used was Universal primer (manufactured by Pharmacia) and the reaction kit used was Auto read sequencing kit (manufactured by Pharmacia). As a result, the plasmids prepared were, as originally designed, all confirmed to be HSA expression vectors controlled by 5'-deleted AOX2 promoter. The HSA expression vector obtained using a primer PCR60 and having an upstream region length from ATG of 803 bp (nucleotide number of 5' endpoint of promoter being 726) was named pHO060; the one obtained using a primer PCR63 and having an upstream region length from ATG of 684 bp (nucleotide number of 5' endpoint of promoter being 845) was named pHO063; the one obtained using a primer PCR64 and having an upstream region length from ATG of 568 bp (nucleotide number of 5' endpoint of promoter being 961) was named pHO064; the one obtained using a primer PCR65 and having an upstream region length from ATG of 462 bp (nucleotide number of 5' endpoint of promoter being 1067) was named pHO065; the one obtained using a primer PCR71 and having an upstream region length from ATG of 341 bp (nucleotide number of 5' endpoint of promoter being 1188) was named pYI071; the one obtained using a primer PCR66 and having an upstream region length from ATG of 273 bp (nucleotide number of 5' endpoint of promoter being 1256) was named pHO066; the one obtained using a primer PCR67 and having an upstream region length from ATG of 248 bp (nucleotide number of 5' endpoint of promoter being 1281) was named pHO067; and the one obtained using a primer PCR68 and having an upstream region length from ATG of 214 bp (nucleotide number of 5' endpoint of promoter being 1315) was named pHO068 (FIG. 8).

EXAMPLE 6

Preparation of *Pichia pastoris* transformant having single copy of HSA expression vector

*Pichia pastoris* GTS115 strain, a host stain, was inoculated to YPD medium (1% yeast extract, 2% peptone, 2% dextrose), and cultured at 30° C. for 1 day. Cells were collected by centrifugation, and washed with sterile water, SED solution (1M sorbitol, 25 mM EDTA, 50 mM dithiothreitol), and 1M sorbitol. The cells were suspended in a zymolyase solution (50 pg/ml zymolyase, 1M sorbitol, 10 mM EDTA, 100 mM sodium citrate, pH 5.8), and cultured at 30° C. for about 20 minutes into protoplast. The protoplast was collected, sequentially washed with 1M sorbitol and CaS solution (1M sorbitol, 10 mM $CaCl_2$), and the cells were suspended in said solution. DNA fragment (10 µg) obtained by digesting HSA expression vector with StuI was added to the cells, and PEG solution (20% PEG 3350, 10 mM $CaCl_2$, 10 mM Tris-HCl, pH 7.4) was added thereto, and the mixture was left standing for about 30 minutes. By this procedure, the vector can be efficiently integrated into *Pichia pastoris* chromosome his4 gene locus. The cells collected by centrifugation were suspended in SOS solution (1M sorbitol, 10 mM $CaCl_2$, 0.3×YPD medium), and layered on a regeneration agar plate together with regeneration agar (1M sorbitol, 1.35% yeast nitrogen base without amino acids, 2% dextrose, 400 µg/ml biotin, 1% agar) kept at 45° C., and cultured at 30° C. for 3 to 5 days. The top layer agar containing the transformant grown was scraped, and the agar was crushed in sterile water to give a cell suspension. The cell suspension was diluted with an appropriate amount of sterile water, and spread on an SD w/o a.a. agar medium (0.7% yeast nitrogen base without amino acids, 2% dextrose, 1.5% agar). After cultivation at 30° C. for several days, the colonies grown were again inoculated on an SD w/o a.a. agar medium to give recombinant clones.

Several clones were inoculated to 2 ml of YPD medium and cultured at 30° C. for 2 to 3 days. The cells collected by centrifugation were washed with 1.2N sorbitol, and suspended in a zymolyase solution (50 mM Tris-HCl, pH 7.5, 1.2M sorbitol, 20 mM 2-mercaptoethanol, 0.4 mg/ml zymolyase). The suspension was cultured at 30° C. into protoplast. The protoplast was suspended in an SDS solution (0.4% SDS, 80 mM Tris-HCl, pH 7.5, 40 mM EDTA), and cultured at 65° C. for lysis. A solution of 5M potassium acetate was added thereto, and the solution was ice-cooled, followed by centrifugation. The supernatant was separated, added with 2.5-fold amount of ethanol, and left standing. After centrifugation, DNA precipitate was dissolved in TE buffer (10 mM Tris-HCl, pH 8.0, 1 mM EDTA). Ribonuclease A was added thereto, and the mixture was cultured at 37° C. and extracted from phenol/chloroform. One-tenth amount of 3M sodium acetate solution and 2.5-fold amount of ethanol were added to the water layer, and the resultant precipitate was dissolved in TE buffer, which was used as a recombinant chromosome DNA solution. The recombinant chromosome DNA solution was digested with BglII and subjected to agarose gel electrophoresis. The agarose gel was stained with ethidium bromide, and treated with 0.2N hydrochloric acid. The gel was treated with an alkali solution (0.2N NaOH, 0.6M NaCl), and then with a neutralizing solution (0.2M Tris-HCl, pH 7.4, 0.6M NaCl). The DNA in the gel was transferred to a nylon membrane in 6× SSC [20× SSC (0.3M trisodium citrate 2 hydrate, 3M NaCl) was diluted by 20/6] by capillary method, and the nylon membrane was used for Southern hybridization using an HSA gene as a probe. The HSA gene probe (0.7 kb) was prepared by digesting an expression vector pMM041 with PstI-BamHI. Labelling of probe, prehybridization, hybridization, washing, immunological detection, and so on were conducted using nonradio system DNA labelling and detection kit (DIG-ELISA) (manufactured by Behringer Mannheim AG) in the manner described in the manual attached to the kit. The clone with 4.5 kb single band by detection was taken as a transformant into which single copy of HSA expression vector had been integrated.

EXAMPLE 7

Figure 9:
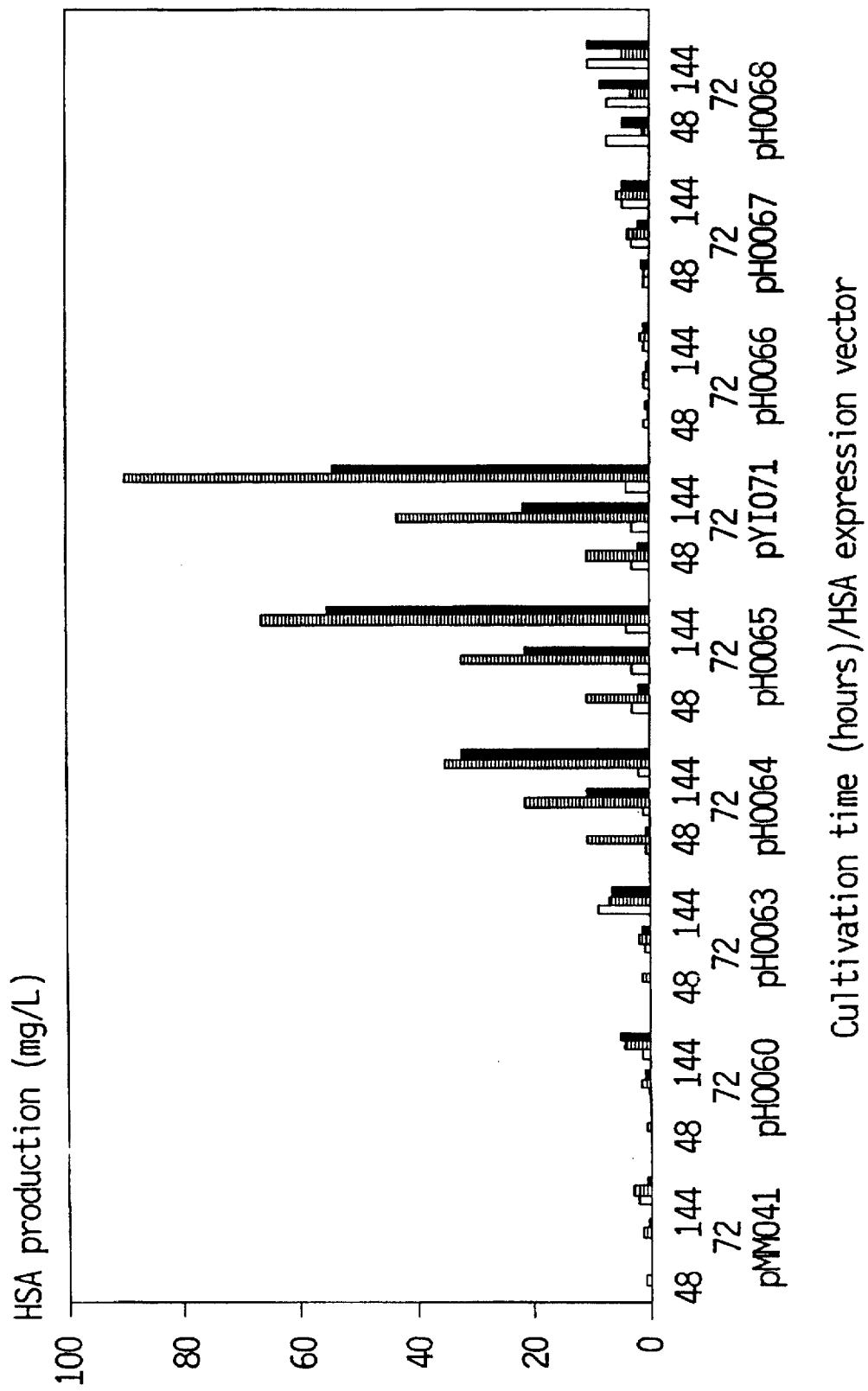
FIG. 9 shows transcription activity and methanol induction of upstream-deleted AOX2 promoters, estimated by cultivating, in YPD medium, YPM medium, or YPDM medium, respective transformants into which each HSA expression vector carrying a specific promoter has been introduced, and measuring HSA production at 48, 72, or 144 hours later, wherein □ is YPD medium, ■ is YPM medium, and ■ is YPDM medium.

Comparison of transcription activity of AOX2 promoter which underwent deletion of 5'-upstream region Transformants into which single copy of each vector had been integrated were subjected to shake culture at 29.5° C.

and 140 rpm in 50 ml of YPD medium, YPM medium (1% yeast extract, 2% peptone, 2% methanol) or YPDM medium (1% yeast extract, 2% peptone, 2% dextrose, 2% methanol). By determining the time-course change of HSA yield, methanol induction and activity of the promoters were compared. In the case of pHO064, pHO065, and pYI071 transformants, high HSA production was attained when methanol was used as a carbon source, whereas the production was repressed when glucose was used as a carbon source. In the case of YPDM medium containing both methanol and glucose, glucose was first consumed, and then methanol to produce HSA. In contrast, transformants pHO063, pHO060, and pMM041, having a long 5'-upstream region, and transformants pHO066, pHO067, and pHO068, having a short 5'-upstream region, showed only weak HSA expression in any of those media. The growth of these transformants was fine, and there could be observed no difference in the degree of growth among the transformants. The time-course change in HSA production is shown in FIG. 9, and the comparison of HSA yield at 144 hours of culture in the YPM medium is given in Table 2.

TABLE 2

Comparison of HSA yield at 144 hours of culture of transformants in YPM medium

| HSA expression vector | Length of AOX2 promoter (bp) | HSA yield (mg/l) |
| --- | --- | --- |
| pMM041 | 1529 | 3 |
| pHO060 | 803 | 5 |
| pHO063 | 684 | 6 |
| pHO064 | 568 | 32 |
| pHO065 | 462 | 60 |
| pYI071 | 341 | 80 |
| pHO066 | 273 | 2 |
| pHO067 | 248 | 5 |
| pHO068 | 214 | 5 |

EXAMPLE 8

Correlation between AOX2 promoter activity and HSA mRNA amount

Figure 10:
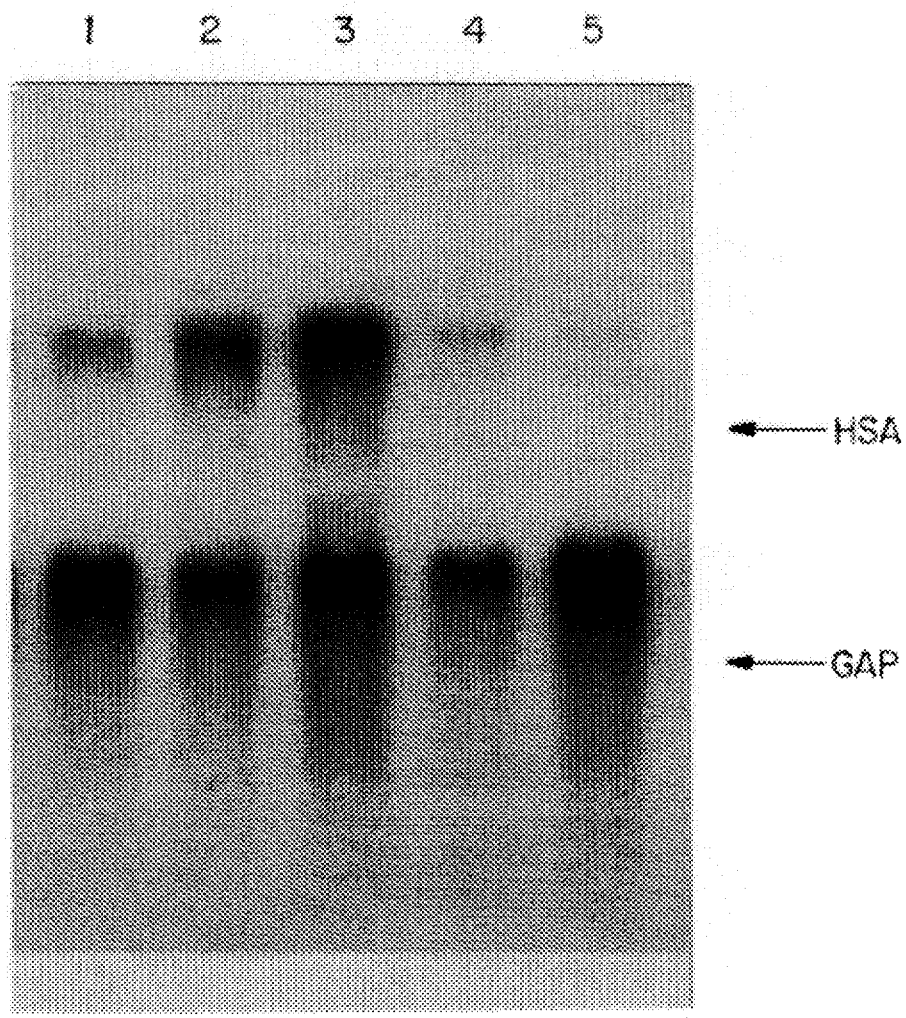
FIG. 10 is a photograph of electrophoresis showing the comparison of HSA mRNA amount (by Northern analysis method) expressed under the control of 4 upstream-deleted AOX2 promoters or natural AOX2 promoter, wherein lane 1 is pHO066 transformant, lane 2 is pYI071 transformant, lane 3 is pHO064 transformant, lane 4 is pHO063 transformant, and lane 5 is pMM041 transformant.

In a 5'-upstream length-dependent manner, promoters showed noticeable difference in HSA production. By the comparison of HSA mRNA amount, it was examined if the difference in production was attributable to the transcription activity of promoters. pMM041 transformant, pHO063 transformant, pHO064 transformant, pYI071 transformant, and pHO066 transformant were respectively cultivated in YPM medium, and mRNA was extracted by guanidine thiocyanate method in the late period of logarithmic growth phase. Using 5 μg of mRNA extracted from each transformant, Northern blotting was conducted using an HSA DNA fragment as a probe, to compare HSA mRNA amount, the result of which is given in FIG. 10. pHO064 transformant and pYI071 transformant which showed high HSA yield also showed high HSA mRNA expression. On the other hand, pMM041 transformant, pHO063 transformant, and pHO066 transformant which showed low HSA yield showed very poor expression level of HSA mRNA. Accordingly, it was suggested that HSA production was dependent on the outcome of the transcription.

Based on the results of Examples 7 and 8, the following was clarified as regards the transcription control mechanism of AOX2 promoter.

As was made clear with pHO063 transformant, the AOX2 promoter comprising a region extending downstream from nucleotide 845 inclusive showed a very weak transcription activity. As was seen with pHO064 transformant, the AOX2 promoter comprising a region extending downstream from nucleotide 961 inclusive showed a markedly strong transcription activity. It is speculated, therefore, a sequence repressing the transcription activity of AOX2 promoter (upstream repression sequence, URS, hereinafter this region is referred to as URS1) exists in a region in nucleotides 845–960.

AOX2 promoter wherein URS1 has been deleted comes to show a (hidden and inherent) strong transcription activity, whereas an AOX2 promoter comprising only a region extending downstream from nucleotide 1256 inclusive and therefore also lacking URS1 shows only a weak transcription expression, as seen with pHO066 transformant. Accordingly, it was speculated that a natural AOX2 promoter comprised a sequence concerned with the enhancement of transcription (upstream activation sequence, hereinafter referred to as UAS) in a region in nucleotides 960–1256. Further, based on the results with pYI071 transformant and pHO066 transformant, UAS supposedly exists between nucleotides 1188 and 1255. UAS is essential for the strong expression of AOX2 promoter.

EXAMPLE 9

Identification of UAS region—1

Figure 11:
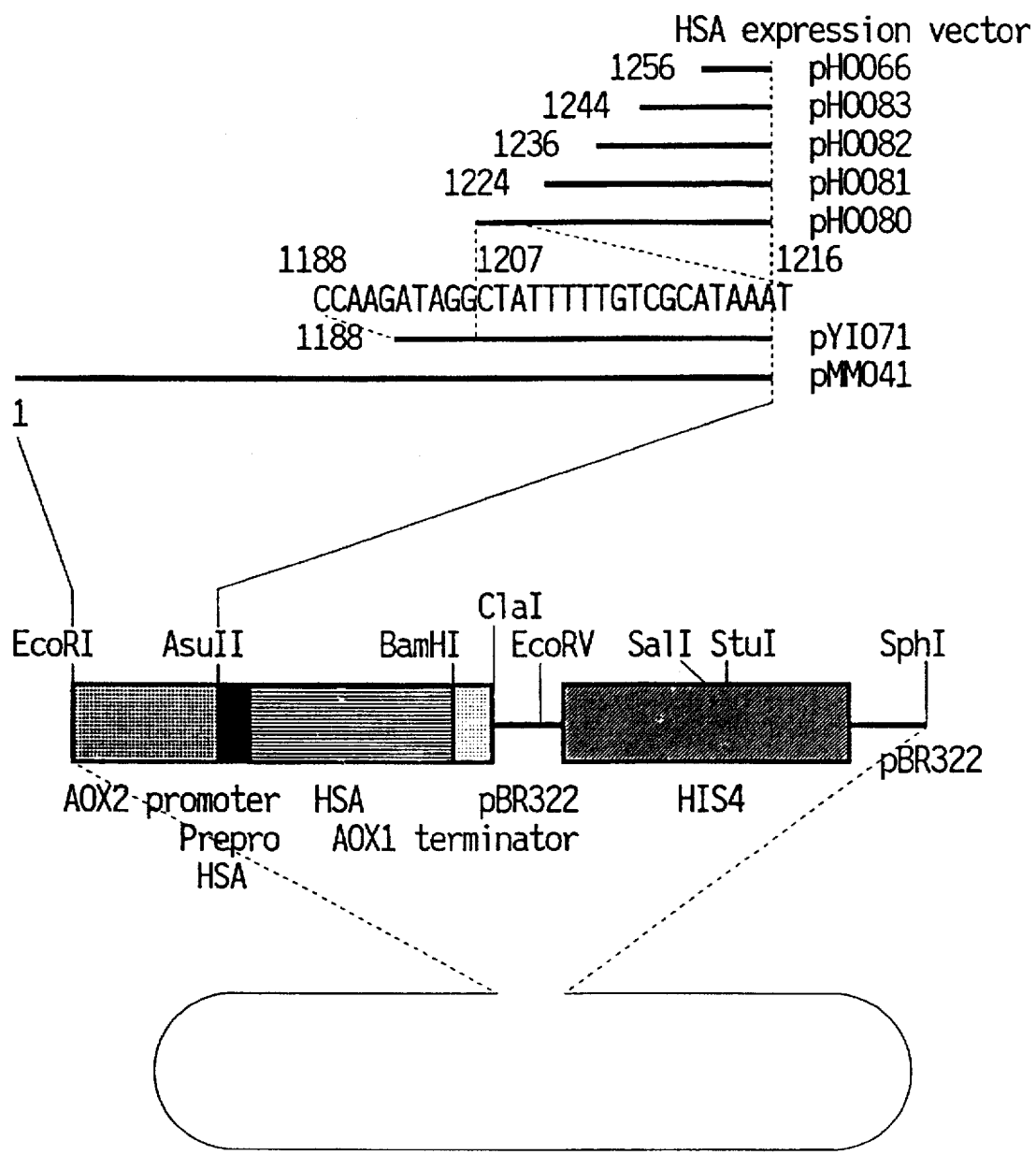
FIG. 11 shows an HSA expression vector used for specifying UAS region.

In Example 7, existence of UAS in a region in nucleotides 1188–1255 of AOX2 promoter was suggested. The inventors tried to further specify the sequence. AOX2 promoter fragments having an upstream region length from the translation initiation codon ATG of from 273 bp to 341 bp, i.e. 322 bp, 305 bp, 293 bp, and 285 bp AOX2 promoter fragments, were amplified by PCR method as in Example 4. The HSA expression vectors carrying them were constructed in the same manner as in Example 5, and named respectively pHO080, pHO081, pHO082, and pHO083 (FIG. 11). Using these vectors, transformants were prepared in the same manner as in Example 6. The transformants were cultured in YPM medium in the same manner as in Example 7 for 72 hours. As a result, only pYI071 transformant made high HSA production, and others made only a low HSA expression, as shown in Table 3.

TABLE 3

Comparison of HSA yield at 72 hours of culture in YPM medium of transformants for UAS analysis −1

| HSA expression vector | Length of AOX2 promoter (bp) | HSA yield (mg/l) |
| --- | --- | --- |
| pYI071 | 341 | 80 |
| pHO080 | 322 | 1 |
| pHO081 | 305 | 1 |
| pHO082 | 293 | 3 |
| pHO083 | 285 | 2 |
| pHO066 | 273 | 1 |

Therefrom it was speculated that the UAS region of AOX2 promoter comprised a part of or the whole of the region between 341 bp and 323 bp upstream from ATG (nucleotides 1188–1206).

EXAMPLE 10

Identification of UAS region—2

Four kinds of site-directed mutation were introduced into regions in nucleotides 1188–1212 of AOX2 promoter by utilizing PCR method, and the influence of the mutation on the transcription activity of the promoter was analyzed.

The introduction of the site-directed mutation by utilizing PCR method followed the method described in a literature (Ito, W., et al, Gene, 102, 67–70, 1991). As the template plasmid, used was plasmid pHO074 obtained by cleaving an AOX2 promoter and about 1.2 kb of the 5'-region of HSA from HSA expression vector pHO065 with EcoRI and PstI, and subcloning same to EcoRI/Pst I site of cloning vector pUC19. Then, four kinds of primers, UASps, for site-directed mutagenesis were synthesized.

Figure 13A:
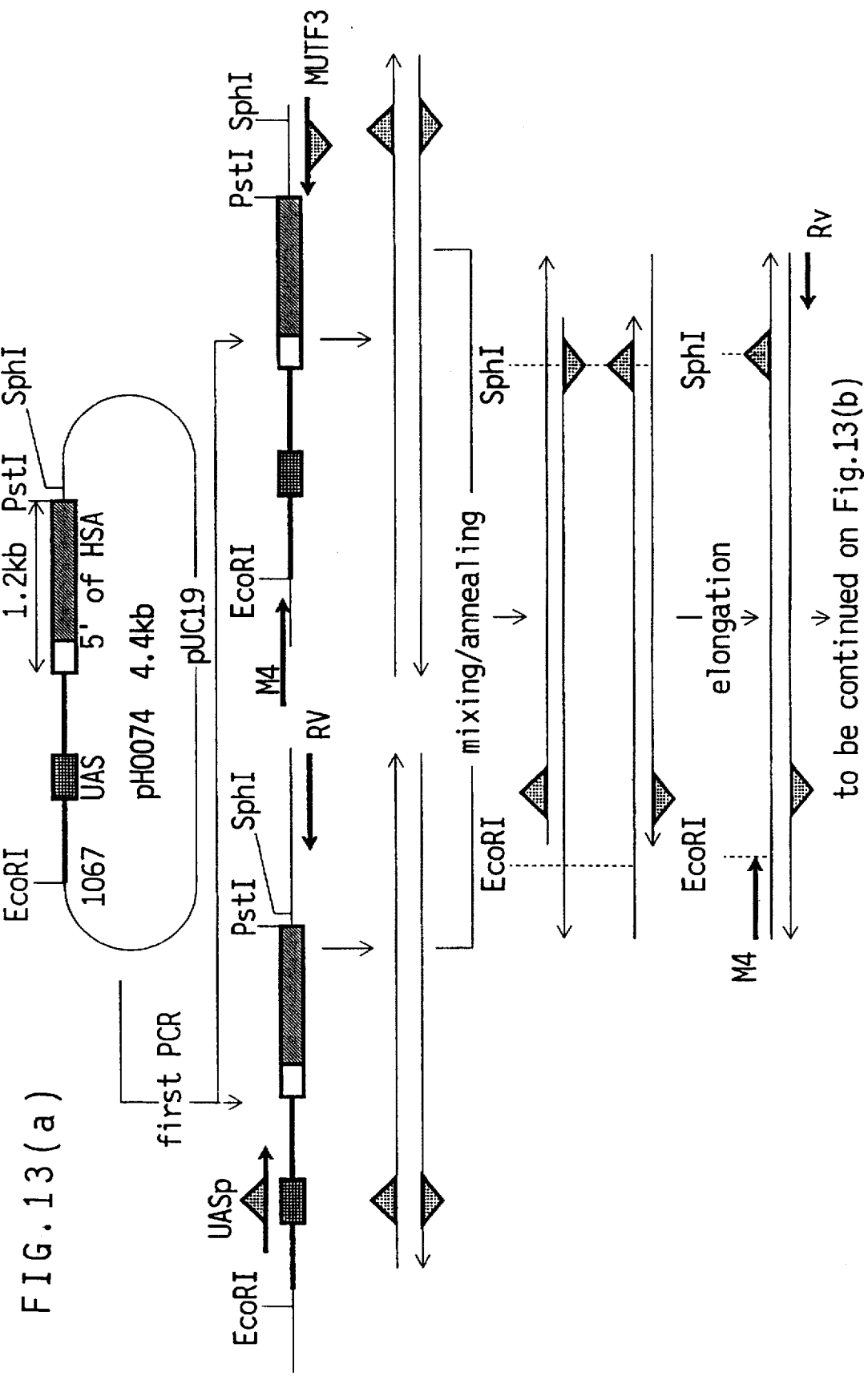
FIG. 13(a) and (b) combined shows the construction of an HSA expression vector carrying AOX2 promoter having a mutant UAS region.
Figure 13B:
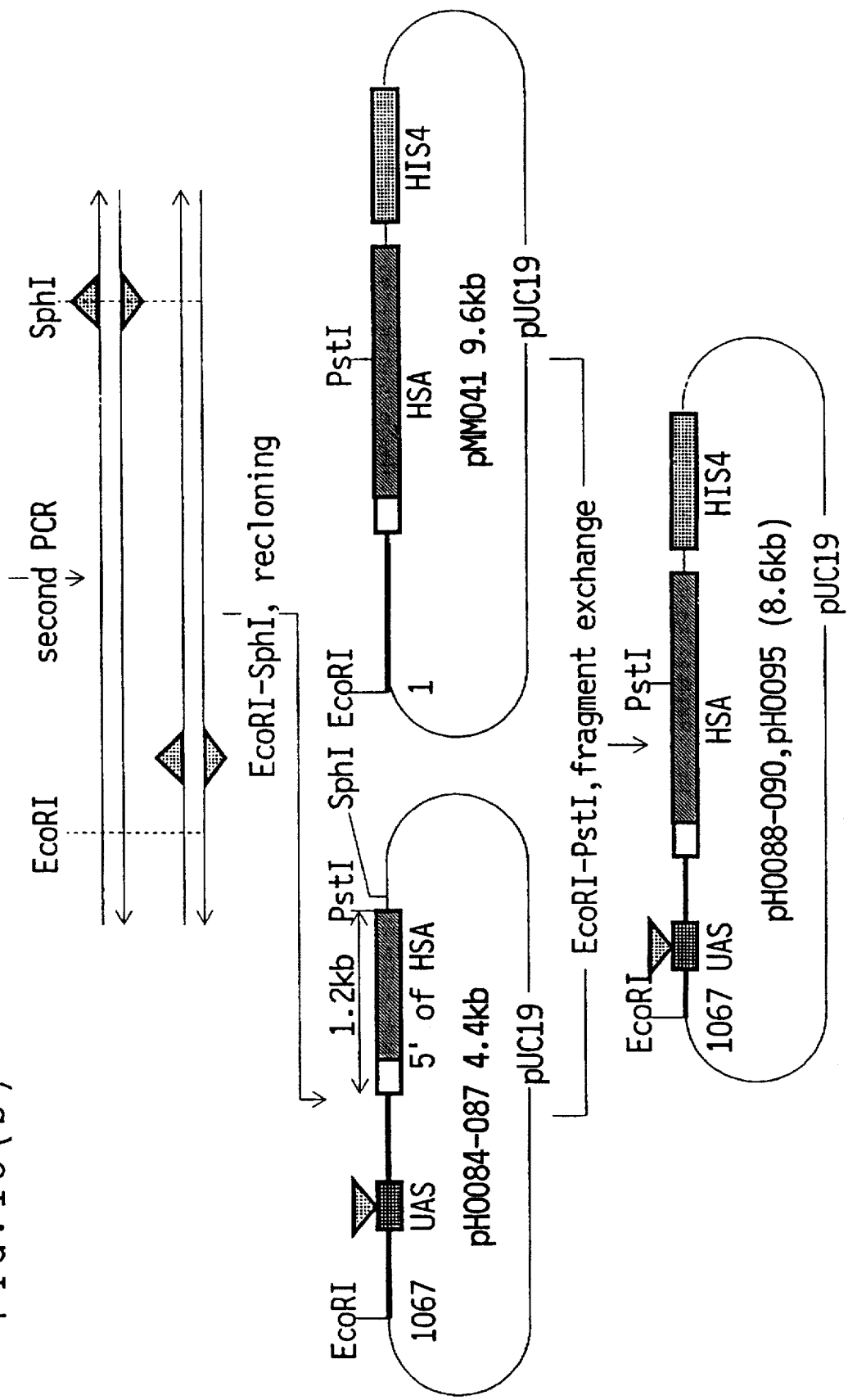

The sequences thereof are given in FIG. 12, and the steps for introducing the mutation are summarized in FIG. 13.

First, each PCR product was prepared using a UASp and a primer RV complementary to the 3' sequence of multi-cloning site (manufactured by Takara Shuzo Kabushiki Kaisha). In addition, PCR products were prepared, in other reaction tubes, using primer M4 (manufactured by Takara Shuzo Kabushiki Kaisha) complementary to the 5' sequence of the multicloning site, and primer MUTF3 (manufactured by Takara Shuzo Kabushiki Kaisha) which was complementary to the 3' sequence of the multicloning site but the sites corresponding to the SphI site and HindIII site of the multicloning site had been deleted by nucleotide replacement. The latter PCR products underwent deletion of the sites corresponding to the SphI site and HindIII site of the multicloning site. After removing low molecular weight substances from the both PCR products, equivalent amounts of the both products were mixed, denatured with heat and cooled for annealing, thereby forming heteroduplexes. The heteroduplexes were completed by polymerase reaction, and a second PCR was conducted using M4 and RV. By this process, two kinds of PCR products can be theoretically obtained, i.e. desired UAS into which mutation has been introduced and one with the sites corresponding to the SphI site and HindIII site of the multicloning sites having been eliminated. Accordingly, the UAS alone into which mutation has been introduced can be obtained by digesting the mixture with EcoRI and SphI and recloning same to EcoRI/SphI of pUC19 upon removal of low molecular substances. The nucleotide sequence of the AOX2 promoters of several kinds of plasmids thus obtained was determined, and AOX2 promoters into which site-directed mutation had been introduced were obtained. The plasmids carrying those were named pHO084, pHO085, pHO086, and pHO087, respectively.

Figure 14:
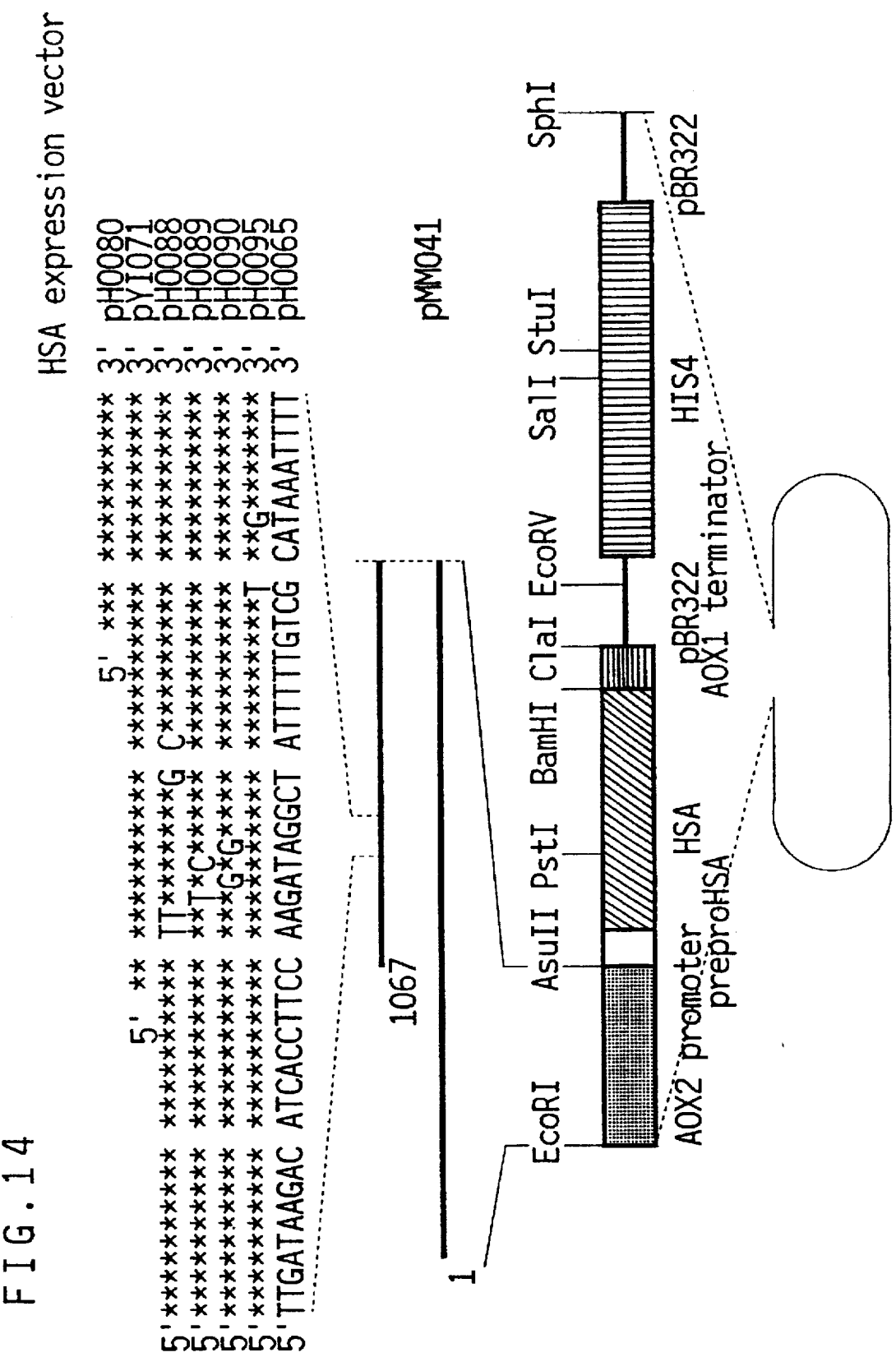
FIG. 14 shows an HSA expression vector under the control of AOX2 promoter having a mutant UAS region (SEQ ID. NO. 26).

The pHOs 084–087 were digested with EcoRI and PstI to give fragments containing a 462 bp AOX2 promoter and about 1.2 kb of 5' region of HSA gene. By exchanging the fragment with about 1170 bp fragment including natural AOX2 promoter and 5' region of HSA gene, which was obtained by digesting HSA expression vector pMM041 with EcoRI and PstI, constructed were HSA expression vectors pHO088, pHO089, pHO090, and pHO095 which were under the control of the site-directedly mutated promoters (FIG. 14).

Using these vectors, transformation was conducted in the same manner as in Example 6 to prepare transformants in which single copy of an HSA expression vector had been integrated. The transformants were cultivated in YPM medium for 72 hours in the same manner as in Example 7. As a result, the transcription activity of all the site-directedly mutated promoters decreased to ¹⁄₄₀ to ⅙ that of the AOX2 promoters (pYI071, pHO065) which presumably included complete UAS but did not comprise URS1 (Table 4). Accordingly, it was speculated that the UAS of AOX2 promoter comprised a part of or the whole of the sequence -CCAAGATAGGCTATTTTTGTCGCAT-3' (SEQ.ID.NO:27) corresponding to nucleotides 1188–1212.

TABLE 4

| HSA expression vector | HSA yield (mg/l) |
|---|---|
| pHO080 | 0.5 |
| pYI071 | 40 |
| pHO088 | 1 |
| pHO089 | 3 |
| pHO090 | 2 |
| pHO095 | 5 |
| pHO065 | 30 |

EXAMPLE 11

Identification of UAS region—3

Should a sequence located at the vicinity of and including nucleotides 1188–1212 functions as a UAS, it suggests a possibility that a sequence homologous with nucleotides 1188–1212 exists in the promoter region of AOX1 gene which is the other alcohol oxydase. Thus, the homology search in the nucleotide sequences of AOX1 promoter to nucleotides 1188–1212 and its vicinity of the AOX2 promoter was conducted to find two homologous sequences in the AOX2 promoter (FIG. 15). The result suggests that the UAS of AOX2 promoter was contained in a region in nucleotides 1192–1216. Then, the corresponding sequence 5'-GATAGGCTATTTTTGTCGCATAAAT-3' (SEQ ID NO: 10) was examined for its function. That is, EcoRI sites were added to the both ends of the 25 bp fragment of nucleotides 1192–1216 which was a putative UAS of AOX2 promoter, and chemically synthesized using DNA/RNA synthesizer (Model 392, manufactured by ABI). The sequences were: plus strand (SEQ. ID NO. 20), 5'-AATTCGATAGGCTATTTTTGTCGCATAAATG-3', reverse strand (SEQ.ID.NO.21), 5'-AATTCATTTATGCGACAAAAATAGCCTATCG-3'. After synthesis, they were purified by an NAP10 column (manufactured by Pharmacia). About 5 μg each of plus strand nucleotide and reverse nucleotide were mixed, heated at 95° C. for 5 minutes, and cooled for annealing. The HSA expression plasmid pHO090 with lowered transcription activity due to the introduction of site-directed mutation into the UAS in Example 10, was digested with EcoRI, and the linear fragment of pHO090 and the aforementioned annealed synthetic DNA fragment were ligated. Using the ligated fragment, E. coli JM109 was transformed. Plasmids were prepared from several transformants, from which a desired plasmid inserted with the putative UAS at EcoRI site was selected by the analysis of restriction enzyme and DNA sequencing, and named HSA expression vector pHO090F. Using this vector or pHO090, transformation was conducted in the same manner as in Example 6 to prepare a transformant in which single copy of pHO090F or pHO090 had been integrated. The transformant was cultivated in YPM medium for 72 hours in the same manner as in Example 7. The transformant of the original vector pHO090 produced HSA at 2 mg/l, while pHO090F transformant produced 10 times more or 20 mg/l of HSA (Table 5). Accordingly, it was suggested that nucleotides 1192–1216 (5'-GATAGGCTATTTTTGTCGCATAAAT-3') (SEQ.ID.NO:10) of AOX2 promoter enhanced transcription activity; namely, the sequence comprised UAS.

17

TABLE 5

Functional analysis of putative UAS

| HSA expression vector | HSA production in culture supernatant (mg/l) |
|---|---|
| pHO090 | 2 |
| pHO090F | 20 |

EXAMPLE 12

Production of AOX2 promoter with mutation in a region in nucleotides 1274–1314

By subculturing a *Pichia pastoris* strain showing poor methanol utilization due to the deletion of the AOX1 gene, in a medium containing methanol as a sole carbon source, a mutant strain showing the growth improved as well as a strain having an AOX1 gene can be obtained. It has been made clear that the mutation occurred in AOX2 promoter results in an improved transcription activity, which in turn causes an improved growth (Japanese Patent Application No. 63598/1991). Using this method, a mutant strain improved in methanol utilization was obtained from an AOX1 -deleted strain. PC4105 strain which is an AOX1- deleted strain was successively subcultured in YPM medium containing methanol as a sole carbon source. The subculture was spread on a YNB w/o a.a.-MeOH agar medium (0.67% yeast nitrogen base without amino acids, 2% methanol, 1.5% agar) at $10^7$–$10^8$ cell/agar medium. The AOX1 deletion strain showed remarkably slow growth, whereas the growth of the mutant strain was fast to the degree that it formed colonies in 3 or 4 days. In this way, mutant strains showing enhanced methanol utilization were obtained from cells subcultured for 20–45 generations, and named SHG4105-4 stain and SHG4105-8 strain.

The AOX2 promoter of the obtained mutant strain was cloned by utilizing PCR method. That is, PCR was performed with the chromosome DNAs of the mutant strain and PC4105 strain using, as a plus strand primer, a DNA fragment (5'-CCGGATCCACTAAGCGAGTCAT CATC-3') (SEQ.ID.NO.22) with BamHI site at the 5'-terminal to hybridize to nucleotides 726–743 of AOX2 promoter, and using, as a reverse strand primer, a DNA fragment (5'-CCGAATTCGACAATATTCTTTGATGC-3') (SEQ.ID.NO.23) with EcoRI site at the 5' terminal to hybridize to nucleotides 1386–1369. The AOX2 promoter fragments amplified as described were cloned into BamHI/EcoRI site of pUC19.

Then, the nucleotide sequence of the AOX2 promoter fragment on the cloning vector was determined. In the parent PC4105 strain, the nucleotide sequence of AOX2 promoter was completely intact. In SHG4105-4 strain, T (1274) of natural AOX2 promoter was replaced with C. In SHG4105-8 strain, T (1274) of natural AOX2 promoter was maintained, but nucleotides 1296–1314 were duplicated once.

EXAMPLE 13

Transcription activity of AOX2 promoters with mutation in a region in nucleotides 1274–1314

Figure 16A:
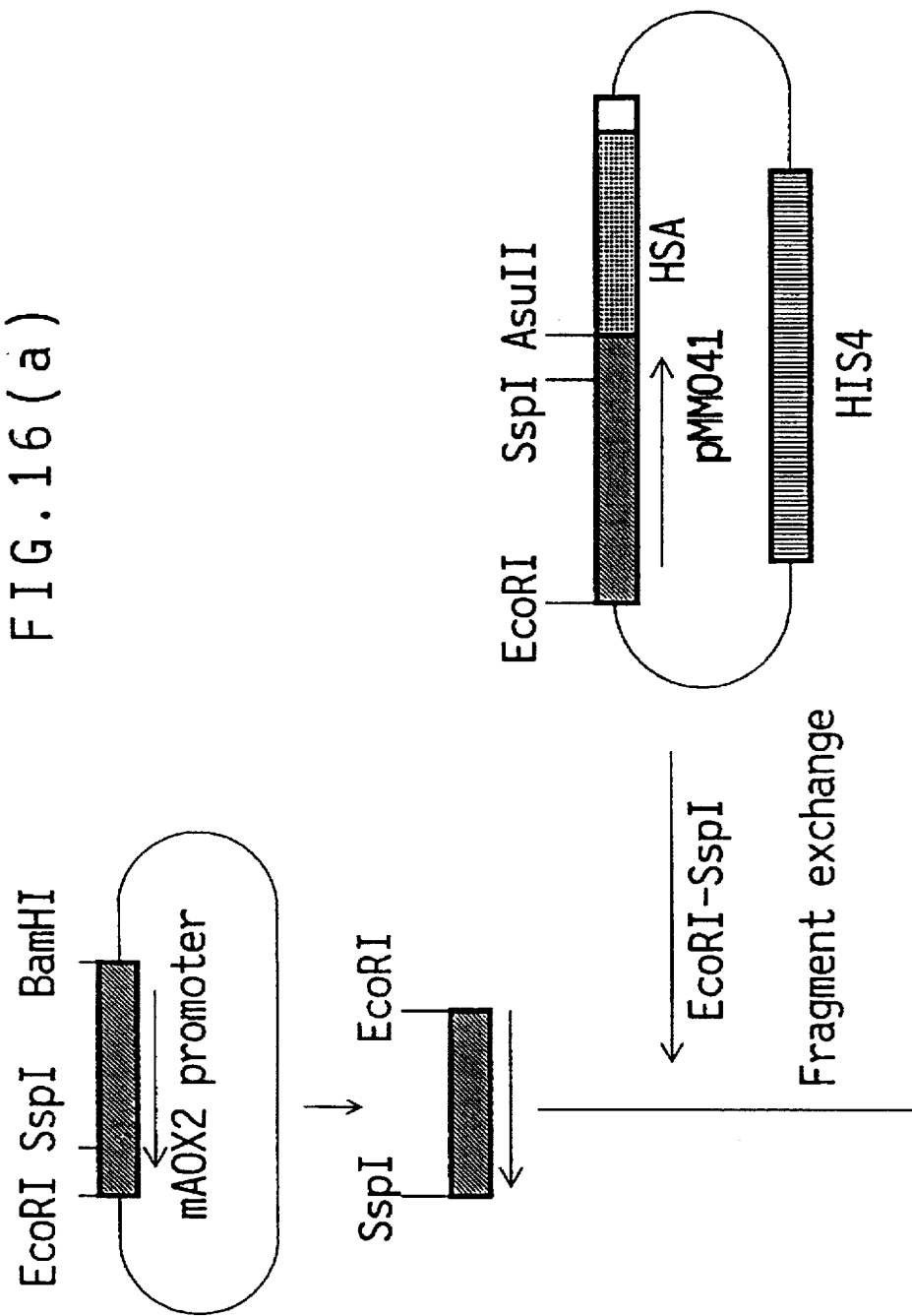
FIG. 16(a) and (b) combined shows an HSA expression vector under the control of AOX2 promoter having mutation in nucleotides 1274–1314 (SEQ ID NO. 1), wherein ▼ is a point mutation at nucleotide (1274) (T→C) and ⇌ is a duplication mutation at nucleotides 1274–1314.
Figure 16B:
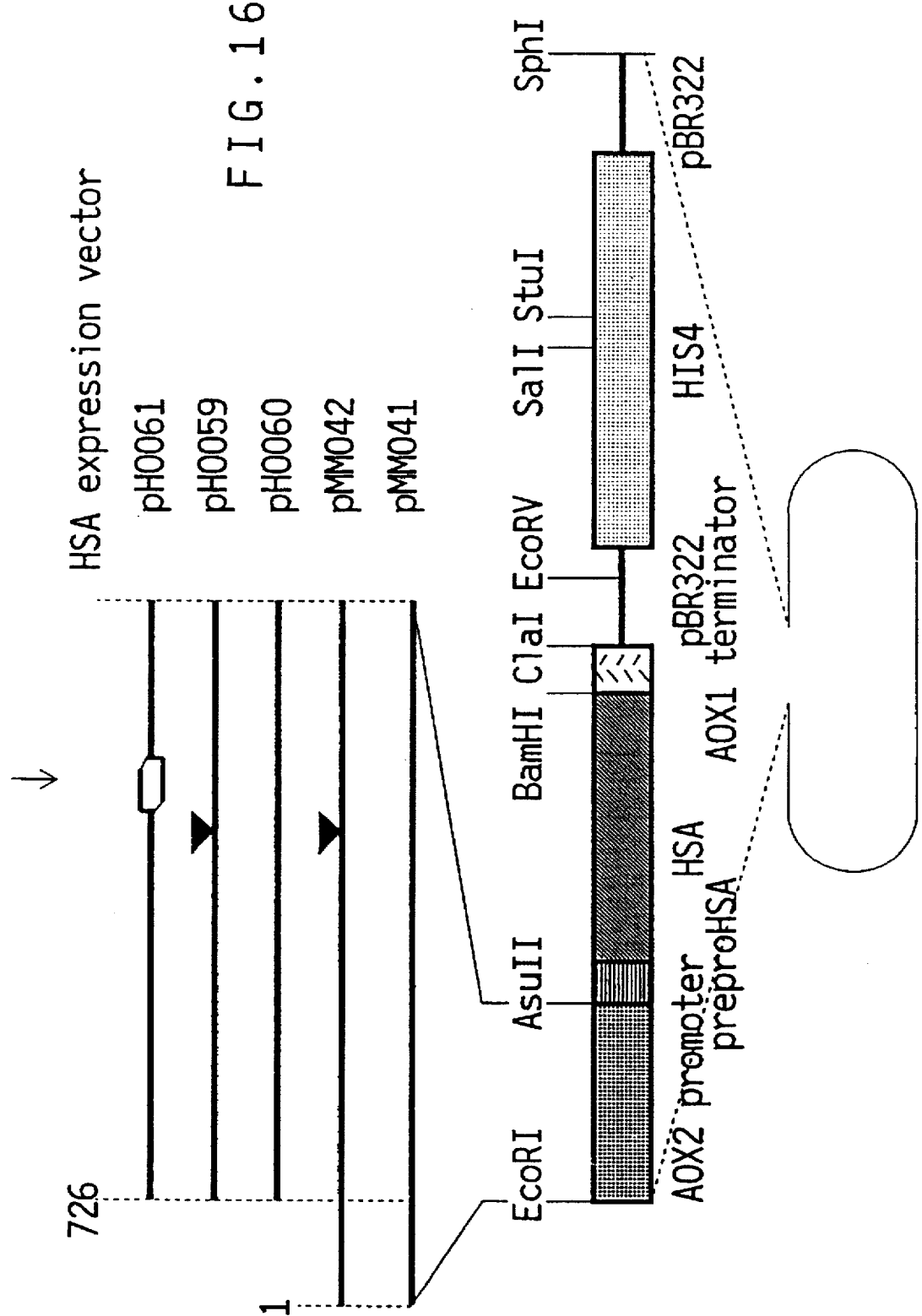

For comparison of transcription activity of cloned mutant AOX2 promoters, vectors allowing HSA expression under the control of these promoters were constructed. First, BamHI site at the 5' terminal of a mutant AOX2 promoter was converted to EcoRI site, and the mutant AOX2 promoter fragments were isolated with EcoRI-SspI. Then, natural AOX2 promoter in HSA expression vector pMM041 was replaced with the mutant AOX2 promoter to give vectors pHO059 (point mutation) and pHO061 (duplication mutation) capable of HSA expression under the control of mutant AOX2 promoter (FIG. 16).

The constructed HSA expression vectors were integrated into the his4 gene locus of the chromosome of *Pichia pastoris* GTS115 strain to prepare transformants in which single copy of each vector had been integrated. The constructed vectors had the length of AOX2 promoter of 803 bp. As the control, used were pHO060 having a natural AOX2 promoter of 803 bp, pMM041 having a natural AOX2 promoter of 1528 bp, and pMM042 having a natural AOX2 promoter of 1528 bp with the replacement of T (1274) with C. Transformants were cultured in YPM medium, and HSA production in the supernatant obtained after 72 hours of culture was measured. pMM041 transformant controlled by natural AOX2 promoter and pHO060 transformant lacking a region extending upstream from nucleotide 726 inclusive exhibited a very low promoter activity and expression of HSA was slight. However, pHO059 transformant controlled by the AOX2 promoter which underwent point mutation at nucleotide 1274 and pHO061 transformant controlled by the AOX2 promoter which underwent duplication mutation showed markedly superior promoter activity and produced HSA in high yields (Table 6).

TABLE 6

Comparison of transcription activity of AOX2 promoter with mutation In a region In nucleotides 1274–1314

| HSA expression vector for transformation | nucleotide No. of 5' endpoint of AOX2 promoter | mutation | HSA production (mg/l) |
|---|---|---|---|
| pMM041 | 1 | natural | 1 |
| pMM042 | 1 | point mutation of T (1274) to C | 60 |
| pHO060 | 726 | natural | 2 |
| pHO059 | 726 | point mutation of T (1274) to C | 60 |
| pHO061 | 726 | duplication of nucleotides 1296–1314 | 40 |

EXAMPLE 8 shows repression of the transcription activity of AOX2 promoter by the presence of URS1. In addition, point mutation of T (1274) to C or duplication mutation of nucleotides 1296–1314 can improve activity of AOX2 promoter even in the presence of URS1, as has been demonstrated with pMM042, pHO059, and pHO061 transformants in Example 12. It was therefore suggested that a region concerned with repression of transcription activity of AOX2 promoter might be present at the region vicinity of and including nucleotides 1274–1314. The region is to be referred as URS2.

EXAMPLE 14

Transcription activity of AOX2 promoter lacking URS1 but having mutant URS2

Figure 17A:
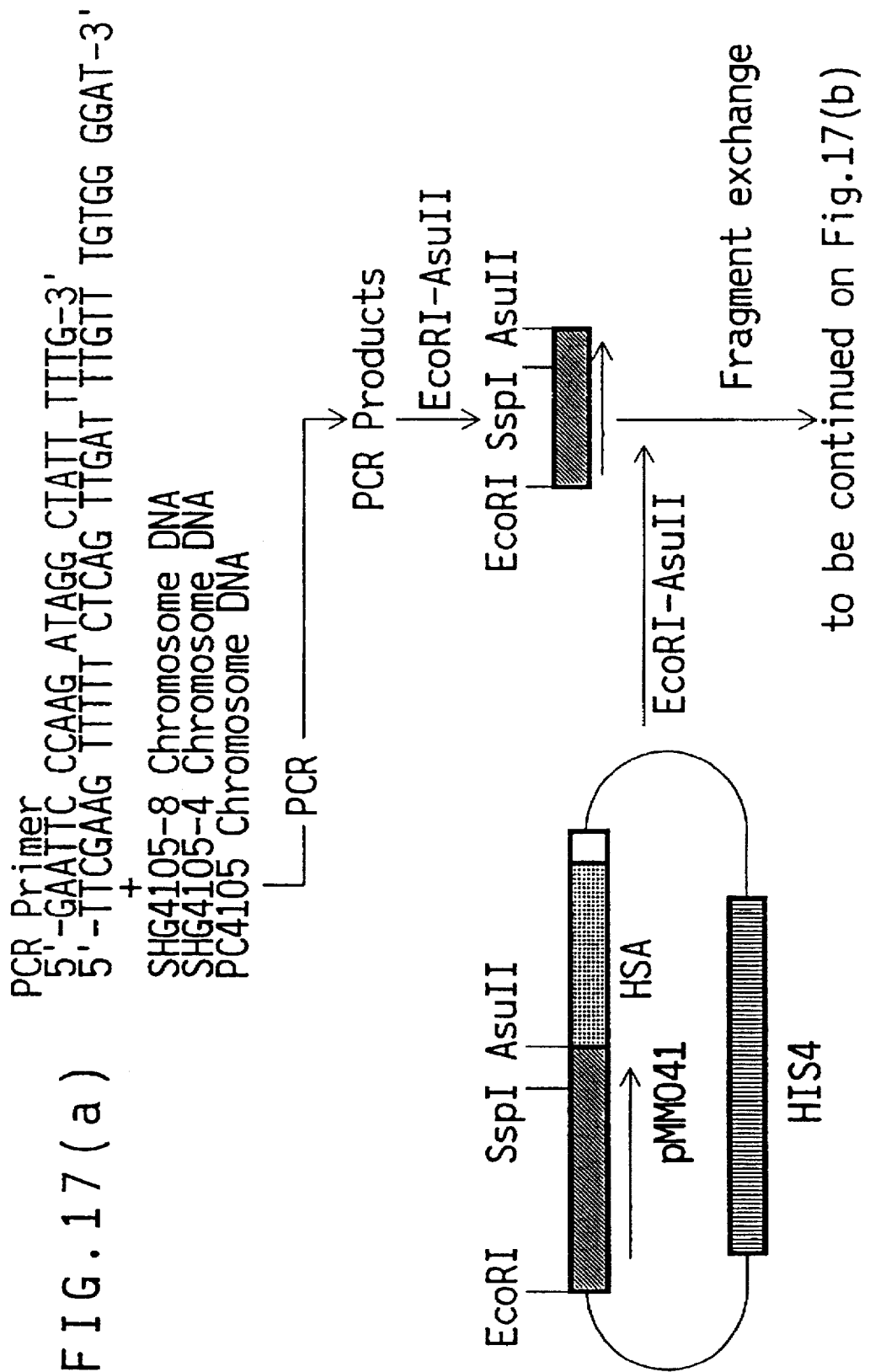
FIG. 17(a) and (b) combined shows an HSA expression vector under the control of AOX2 promoter, wherein URS1 has been deleted and URS2 has been mutated. In the Figure, ▼ is a point mutation at nucleotide (1274) (T→C) and ⇌ is a duplication mutation at nucleotides 1274–1314 (SEQ ID NOS. 30–31).
Figure 17B:
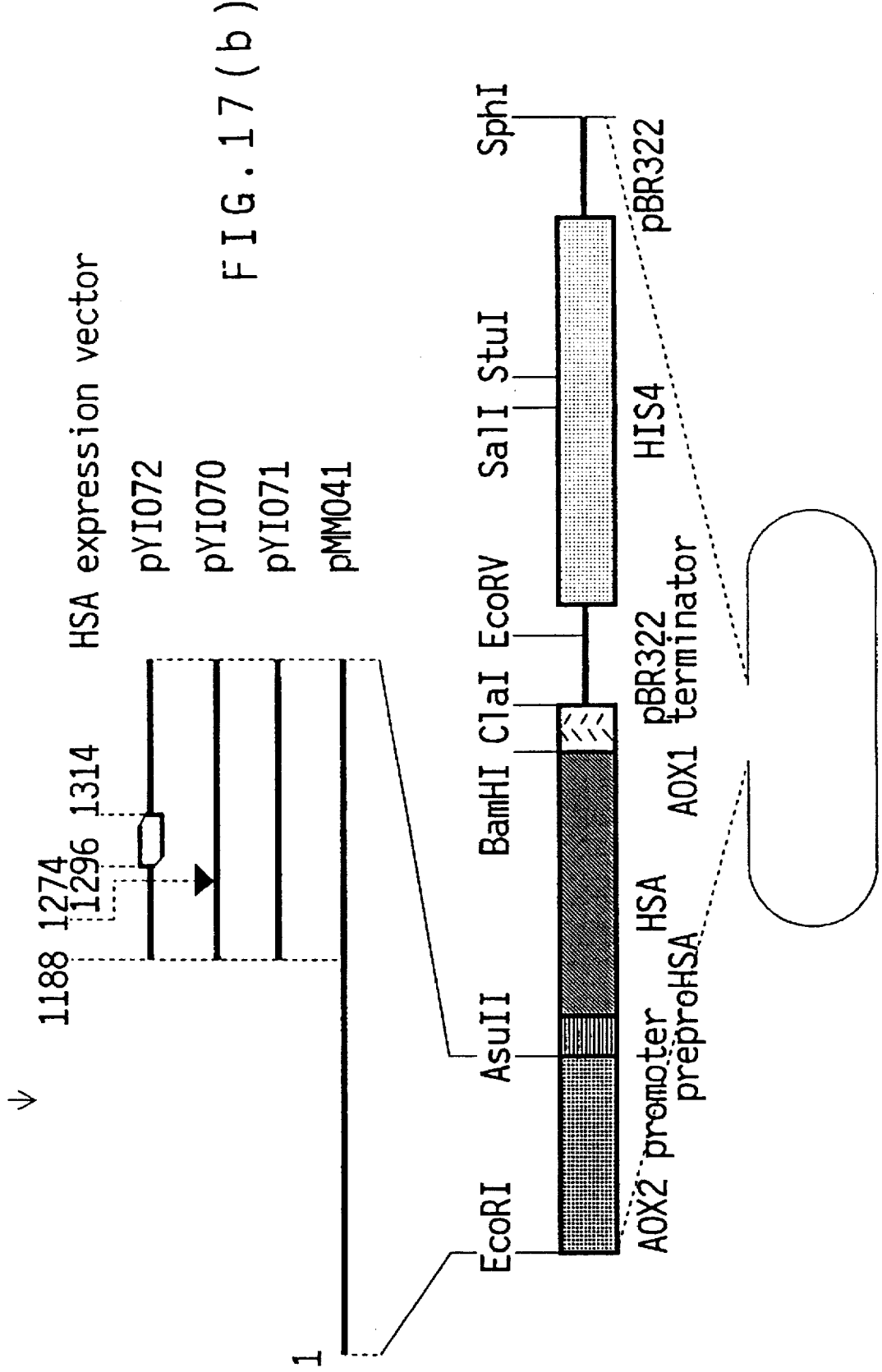

Chromosome DNAs of SHG4105-4 strain having an AOX2 promoter which underwent point mutation at nucleotide 1274, SHG4105-8 strain having a duplication mutation of nucleotides 1296–1314, and GTS115 strain having natural AOX2 promoter were respectively subjected to PCR using, as a plus strand primer, a DNA fragment (5'-GAATTCCCAAGATAGGCTATTTTTG-3') (SEQ.ID.NO.24) with EcoRI site at the 5' terminal to hybridize to nucleotides 1188–1206 of AOX2 promoter, and using, as a reverse strand primer, a DNA fragment (5'-TTCGAAGTTTTTCTCAGTTGATTTGTTTGTGGGAT-3') (SEQ.ID.NO.25) with AsuII site at the 5' terminal to hybridize to nucleotides 1529–1501. Since the DNA fragments amplified as described do not have a region extending upstream from nucleotide 1187 inclusive, they lack URS1, but maintain UAS. After digestion of the DNA fragments with EcoRI and AsaII, natural AOX2 promoter of HSA expression vector pMM041 was replaced with them to give vectors pYI070 (point mutation), pYI072 (deplication mutation), and pYI071 (natural type) (FIG. 17). The constructed HSA expression vectors were integrated into the his4 gene locus of the chromosome of *Pichia pastoris* GTS115 strain to prepare transformants in which single copy of each vector had been integrated. Transformants were cultured in YPM medium, and HSA production in the supernatant after 72 hours of culture was measured. pYI070 transformant and pYI072 transformant showed higher HSA production than did pYI071 transformant. In other words, a promoter lacking URS1 but having mutant URS2 shows higher transcription activity than does a promoter lacking only URS1 (Table 7).

TABLE 7

Comparison of transcription activity of AOX2 promoter lacking URS1 but having mutant URS2

| HSA expression vector for transformation | mutation | HSA production (mg/l) |
|---|---|---|
| pYI071 | natural | 40 |
| pYI070 | point mutation of T (1274) to C | 80 |

TABLE 7-continued

Comparison of transcription activity of AOX2 promoter lacking URS1 but having mutant URS2

| HSA expression vector for transformation | mutation | HSA production (mg/l) |
|---|---|---|
| pYI072 | duplication of nucleotides 1296–1314 | 80 |

Figure 18A:
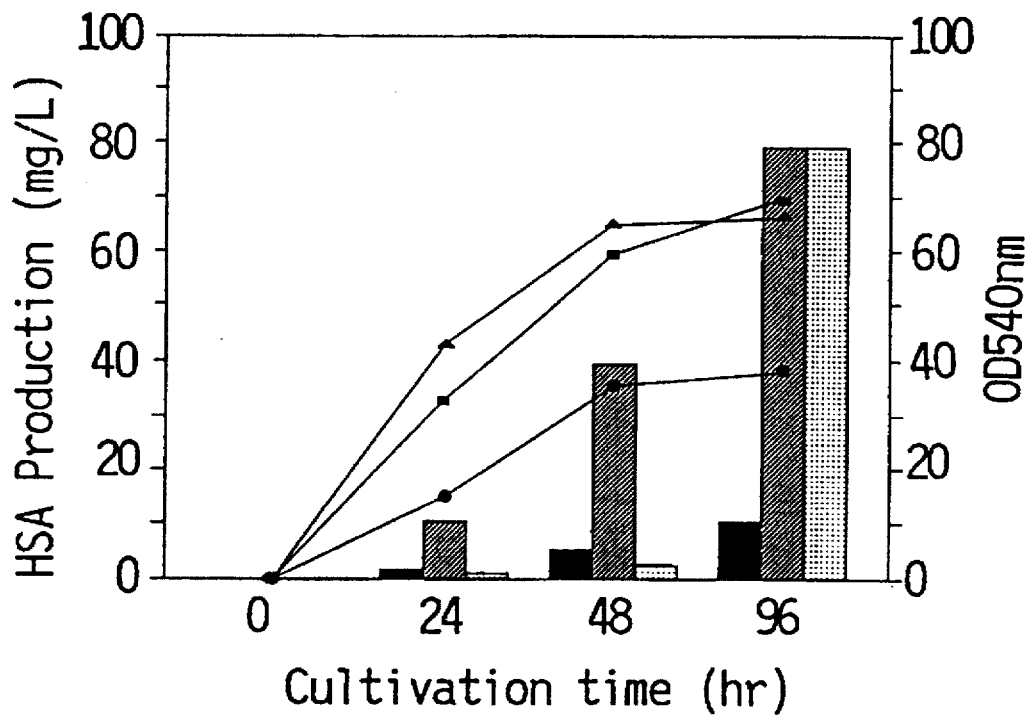
FIG. 18(a) and (b) combined represents methanol induction and glucose repression of URS1-deleted AOX2 promoter and UAS2-mutant AOX2 promoter. In the Figure.
Figure 18B:
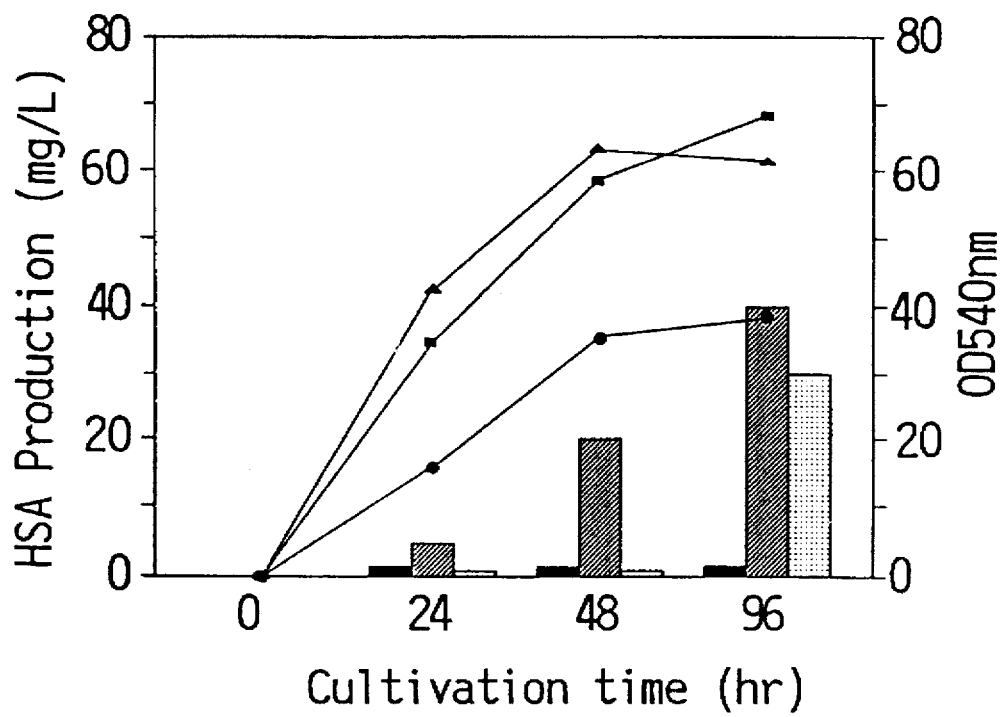

Furthermore, methanol induction and glucose repression of these promoters were examined. The transformants were cultured in YPD medium, YPM medium, or YPDM medium containing both methanol and glucose, and the degree of growth and time-course change in HSA production were measured for 96 hours at predetermined time intervals. As a result, it was found that these mutant promoters were all methanol-inductive and glucose-repressive, and HSA expression was not induced before complete consumption of glucose even in the presence of methanol (FIG. 18).

The mutant AOX2 promoter obtained in the present invention has remarkably enhanced promoter activity as compared with natural AOX2 promoter. Accordingly, the promoter of the invention is highly useful as a promoter to be carried in an expression vector allowing heterologous protein expression. Also, the vector and the transformant of the invention can efficiently express and produce various useful heterologous proteins.

What is claimed is:

1. A method for expressing an isolated structural gene comprising:
   (a) transforming Pichia pastoris with a recombinant vector comprising, in operative linkage:
      (1) a mutant AOX2 promoter; and
      (2) said isolated structural gene, wherein said mutant AOX2 promoter is obtained by mutating a natural AOX2 promoter (SEQ ID NO: 1) so that said mutant AOX2 promoter comprises at least one of the following mutations:
         (i) a deletion of bases from 845 to 960, inclusive;
         (ii) at least one of a base substitution within or insertion within or adjacent bases 1274–1314; said mutated promoter containing bases 1192–1216, inclusive;
   (b) propagating the transformed Pichia pastoris of step (a) under conditions suitable for expression of said isolated structural gene; and
   (c) recovering protein produced by expression of said isolated structural gene.

2. The method of claim 1, wherein said mutant AOX2 promoter is obtained by deleting nucleotides 749–1187.

3. The method of claim 1, wherein said mutant AOX2 promoter is obtained by deleting nucleotides 845–1187.

4. The method of claim 1, wherein said mutant AOX2 promoter is obtained by substituting C for T at nucleotide 1274 and deleting nucleotides 845–1187.

5. The method of claim 1, wherein said mutant AOX2 promoter is obtained by duplicating nucleotides 1296–1314 to form a tandem duplication.

6. The method of claim 1, wherein said mutant AOX2 promoter is obtained by duplicating nucleotides 1296–1314 to form a tandem duplication and deleting nucleotides 845–1187.

7. The method of claim 1, wherein said recombinant vector further comprises in operative linkage a polynucleotide encoding a signal peptide.

8. The method of claim 1, wherein said isolated structural gene encodes albumin.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
( A ) LENGTH: 1528 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
AATTCTTTTT TTCAGACCAT ATGACCGGTC CATCTTCTAC GGGGGGATTA TCTATGCTTT        60

GACCTCTATC TTGATTCTTT TATGATTCAA ATCACTTTTA CGTTATTTAT TACTTACTGG       120

TTATTTACTT AGCGCCTTTT CTGAAAAACA TTTACTAAAA ATCATACATC GGCACTCTCA       180

AACACGACAG ATTGTGATCA AGAAGCAGAG ACAATCACCA CTAAGGTTGC ACATTTGAGC       240

CAGTAGGCTC CTAATAGAGG TTCGATACTT ATTTGATAA  TACGACATAT TGTCTTACCT       300

CTGAATGTGT CAATACTCTC TCGTTCTTCG TCTCGTCAGC TAAAAATATA ACACTTCGAG       360

TAAGATACGC CCAATTGAAG GCTACGAGAT ACCAGACTAT CACTAGTAGA ACTTTGACAT       420

CTGCTAAAGC AGATCAAATA TCCATTTATC CAGAATCAAT TACCTTCCTT TAGCTTGTCG       480
```

| | | | | | |
|---|---|---|---|---|---|
| AAGGCATGAA | AAAGCTACAT | GAAAATCCCC | ATCCTTGAAG | TTTTGTCAGC | TTAAAGGACT | 540
| CCATTTCCTA | AAATTTCAAG | CAGTCCTCTC | AACTAAATTT | TTTTCCATTC | CTCTGCACCC | 600
| AGCCCTCTTC | ATCAACCGTC | CAGCCTTCTC | AAAAGTCCAA | TGTAAGTAGC | CTGCAAATTC | 660
| AGGTTACAAC | CCCTCAATTT | TCCATCCAAG | GGCGATCCTT | ACAAAGTTAA | TATCGAACAG | 720
| CAGAGACTAA | GCGAGTCATC | ATCACCACCC | AACCATGGTG | AAAAACTTTA | ACCATAGATT | 780
| GATGGAGGGT | GTATGGCACT | GGCGGCTGC | ATTAGAGTTT | GAAACTATGG | GGTAATACAT | 840
| CACATCCGGA | ACTGATCCCA | CTCCGAGATC | ATATGCAAAG | CACGTGATGT | ACCCCGTAAA | 900
| CTGCTCGGAT | TATCGTTGCA | ATTCATCGTC | TTAAACAGTA | CAAGAAACTT | TATTCATGGG | 960
| TCATTGGACT | CTGATGAGGG | GCACATTTCC | CCAATGATTT | TTGGGAAAG | AAAGCCGTAA | 1020
| GAGGACAGTT | AAGCGAAAGA | GACAAGACAA | CGAACAGCAA | AAGTGACAGC | TGTCAGCTAC | 1080
| CTAGTGGACA | GTTGGGAGTT | TCCAATTGGT | TGGTTTGAA | TTTTACCCA | TGTTGAGTTG | 1140
| TCCTTGCTTC | TCCTTGCAAA | CAATGCAAGT | TGATAAGACA | TCACCTTCCA | AGATAGGCTA | 1200
| TTTTGTCGC | ATAAATTTT | GTCTCGGAGT | GAAAACCCCT | TTTATGTGAA | CAGATTACAG | 1260
| AAGCGTCCTA | CCCTTCACCG | GTTGAGATGG | GGAGAAAATT | AAGCGATGAG | GAGACGATTA | 1320
| TTGGTATAAA | AGAAGCAACC | AAAATCCCTT | ATTGTCCTTT | TCTGATCAGC | ATCAAAGAAT | 1380
| ATTGTCTTAA | AACGGGCTTT | TAACTACATT | GTTCTTACAC | ATTGCAAACC | TCTTCCTTCT | 1440
| ATTTCGGATC | AACTGTATTG | ACTACATTGA | TCTTTTTTAA | CGAAGTTTAC | GACTTACTAA | 1500
| ATCCCCACAA | ACAAATCAAC | TGAGAAAA | | | | 1528

(2) INFORMATION FOR SEQ ID NO:2:

(i) SEQUENCE CHARACTERISTICS:
        (A) LENGTH: 1089 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

| | | | | | |
|---|---|---|---|---|---|
| AATTCTTTTT | TTCAGACCAT | ATGACCGGTC | CATCTTCTAC | GGGGGGATTA | TCTATGCTTT | 60
| GACCTCTATC | TTGATTCTTT | TATGATTCAA | ATCACTTTTA | CGTTATTTAT | TACTTACTGG | 120
| TTATTTACTT | AGCGCCTTTT | CTGAAAAACA | TTTACTAAAA | ATCATACATC | GGCACTCTCA | 180
| AACACGACAG | ATTGTGATCA | AGAAGCAGAG | ACAATCACCA | CTAAGGTTGC | ACATTTGAGC | 240
| CAGTAGGCTC | CTAATAGAGG | TTCGATACTT | ATTTTGATAA | TACGACATAT | TGTCTTACCT | 300
| CTGAATGTGT | CAATACTCTC | TCGTTCTTCG | TCTCGTCAGC | TAAAAATATA | ACACTTCGAG | 360
| TAAGATACGC | CCAATTGAAG | GCTACGAGAT | ACCAGACTAT | CACTAGTAGA | ACTTTGACAT | 420
| CTGCTAAAGC | AGATCAAATA | TCCATTTATC | CAGAATCAAT | TACCTTCCTT | TAGCTTGTCG | 480
| AAGGCATGAA | AAAGCTACAT | GAAAATCCCC | ATCCTTGAAG | TTTTGTCAGC | TTAAAGGACT | 540
| CCATTTCCTA | AAATTTCAAG | CAGTCCTCTC | AACTAAATTT | TTTTCCATTC | CTCTGCACCC | 600
| AGCCCTCTTC | ATCAACCGTC | CAGCCTTCTC | AAAAGTCCAA | TGTAAGTAGC | CTGCAAATTC | 660
| AGGTTACAAC | CCCTCAATTT | TCCATCCAAG | GGCGATCCTT | ACAAAGTTAA | TATCGAACAG | 720
| CAGAGACTAA | GCGAGTCATC | ATCACCACCC | AAGATAGGCT | ATTTTGTCG | CATAAATTTT | 780
| TGTCTCGGAG | TGAAAACCCC | TTTTATGTGA | ACAGATTACA | GAAGCGTCCT | ACCCTTCACC | 840
| GGTTGAGATG | GGGAGAAAAT | TAAGCGATGA | GGAGACGATT | ATTGGTATAA | AAGAAGCAAC | 900
| CAAAATCCCT | TATTGTCCTT | TTCTGATCAG | CATCAAAGAA | TATTGTCTTA | AAACGGGCTT | 960

| TTAACTACAT | TGTTCTTACA | CATTGCAAAC | CTCTTCCTTC | TATTTCGGAT | CAACTGTATT | 1020 |
| GACTACATTG | ATCTTTTTTA | ACGAAGTTTA | CGACTTACTA | AATCCCCACA | AACAAATCAA | 1080 |
| CTGAGAAAA | | | | | | 1089 |

( 2 ) INFORMATION FOR SEQ ID NO:3:

( i ) SEQUENCE CHARACTERISTICS:
        ( A ) LENGTH: 568 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

| TCATTGGACT | CTGATGAGGG | GCACATTTCC | CCAATGATTT | TTTGGGAAAG | AAAGCCGTAA | 60 |
| GAGGACAGTT | AAGCGAAAGA | GACAAGACAA | CGAACAGCAA | AAGTGACAGC | TGTCAGCTAC | 120 |
| CTAGTGGACA | GTTGGGAGTT | TCCAATTGGT | TGGTTTTGAA | TTTTTACCCA | TGTTGAGTTG | 180 |
| TCCTTGCTTC | TCCTTGCAAA | CAATGCAAGT | TGATAAGACA | TCACCTTCCA | AGATAGGCTA | 240 |
| TTTTTGTCGC | ATAAATTTTT | GTCTCGGAGT | GAAAACCCCT | TTATGTGAA | CAGATTACAG | 300 |
| AAGCGTCCTA | CCCTTCACCG | GTTGAGATGG | GGAGAAAATT | AAGCGATGAG | GAGACGATTA | 360 |
| TTGGTATAAA | AGAAGCAACC | AAAATCCCTT | ATTGTCCTTT | TCTGATCAGC | ATCAAAGAAT | 420 |
| ATTGTCTTAA | AACGGGCTTT | TAACTACATT | GTTCTACAC | ATTGCAAACC | TCTTCCTTCT | 480 |
| ATTTCGGATC | AACTGTATTG | ACTACATTGA | TCTTTTTAA | CGAAGTTTAC | GACTTACTAA | 540 |
| ATCCCCACAA | ACAAATCAAC | TGAGAAAA | | | | 568 |

( 2 ) INFORMATION FOR SEQ ID NO:4:

( i ) SEQUENCE CHARACTERISTICS:
        ( A ) LENGTH: 341 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

| CCAAGATAGG | CTATTTTTGT | CGCATAAATT | TTTGTCTCGG | AGTGAAAACC | CCTTTTATGT | 60 |
| GAACAGATTA | CAGAAGCGTC | CTACCCTTCA | CCGGTTGAGA | TGGGAGAAA | ATTAAGCGAT | 120 |
| GAGGAGACGA | TTATTGGTAT | AAAAGAAGCA | ACCAAAATCC | CTTATTGTCC | TTTTCTGATC | 180 |
| AGCATCAAAG | AATATTGTCT | TAAAACGGGC | TTTTAACTAC | ATTGTTCTTA | CACATTGCAA | 240 |
| ACCTCTTCCT | TCTATTTCGG | ATCAACTGTA | TTGACTACAT | TGATCTTTTT | TAACGAAGTT | 300 |
| TACGACTTAC | TAAATCCCCA | CAAACAAATC | AACTGAGAAA | A | | 341 |

( 2 ) INFORMATION FOR SEQ ID NO:5:

( i ) SEQUENCE CHARACTERISTICS:
        ( A ) LENGTH: 1528 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

| AATTCTTTTT | TTCAGACCAT | ATGACCGGTC | CATCTTCTAC | GGGGGGATTA | TCTATGCTTT | 60 |

-continued

| | | | | | | |
|---|---|---|---|---|---|---|
|GACCTCTATC|TTGATTCTTT|TATGATTCAA|ATCACTTTTA|CGTTATTTAT|TACTTACTGG|120|
|TTATTTACTT|AGCGCCTTTT|CTGAAAAACA|TTTACTAAAA|ATCATACATC|GGCACTCTCA|180|
|AACACGACAG|ATTGTGATCA|AGAAGCAGAG|ACAATCACCA|CTAAGGTTGC|ACATTTGAGC|240|
|CAGTAGGCTC|CTAATAGAGG|TTCGATACTT|ATTTTGATAA|TACGACATAT|TGTCTTACCT|300|
|CTGAATGTGT|CAATACTCTC|TCGTTCTTCG|TCTCGTCAGC|TAAAAATATA|ACACTTCGAG|360|
|TAAGATACGC|CCAATTGAAG|GCTACGAGAT|ACCAGACTAT|CACTAGTAGA|ACTTTGACAT|420|
|CTGCTAAAGC|AGATCAAATA|TCCATTTATC|CAGAATCAAT|TACCTTCCTT|TAGCTTGTCG|480|
|AAGGCATGAA|AAAGCTACAT|GAAAATCCCC|ATCCTTGAAG|TTTTGTCAGC|TTAAAGGACT|540|
|CCATTTCCTA|AAATTTCAAG|CAGTCCTCTC|AACTAAATTT|TTTTCCATTC|CTCTGCACCC|600|
|AGCCCTCTTC|ATCAACCGTC|CAGCCTTCTC|AAAAGTCCAA|TGTAAGTAGC|CTGCAAATTC|660|
|AGGTTACAAC|CCCTCAATTT|TCCATCCAAG|GGCGATCCTT|ACAAAGTTAA|TATCGAACAG|720|
|CAGAGACTAA|GCGAGTCATC|ATCACCACCC|AACGATGGTG|AAAAACTTTA|AGCATAGATT|780|
|GATGGAGGGT|GTATGGCACT|TGGCGGCTGC|ATTAGAGTTT|GAAACTATGG|GGTAATACAT|840|
|CACATCCGGA|ACTGATCCCA|CTCCGAGATC|ATATGCAAAG|CACGTGATGT|ACCCCGTAAA|900|
|CTGCTCGGAT|TATCGTTGCA|ATTCATCGTC|TTAAACAGTA|CAAGAAACTT|TATTCATGGG|960|
|TCATTGGACT|CTGATGAGGG|GCACATTTCC|CCAATGATTT|TTTGGGAAAG|AAAGCCGTAA|1020|
|GAGGACAGTT|AAGCGAAAGA|GACAAGACAA|CGAACAGCAA|AAGTGACAGC|TGTCAGCTAC|1080|
|CTAGTGGACA|GTTGGGAGTT|TCCAATTGGT|TGGTTTTGAA|TTTTACCCA|TGTTGAGTTG|1140|
|TCCTTGCTTC|TCCTTGCAAA|CAATGCAAGT|TGATAAGACA|TCACCTTCCA|AGATAGGCTA|1200|
|TTTTTGTCGC|ATAAATTTTT|GTCTCGGAGT|GAAAACCCCT|TTTATGTGAA|CAGATTACAG|1260|
|AAGCGTCCTA|CCCCTCACCG|GTTGAGATGG|GGAGAAAATT|AAGCGATGAG|GAGACGATTA|1320|
|TTGGTATAAA|AGAAGCAACC|AAAATCCCTT|ATTGTCCTTT|TCTGATCAGC|ATCAAAGAAT|1380|
|ATTGTCTTAA|AACGGGCTTT|TAACTACATT|GTTCTTACAC|ATTGCAAACC|TCTTCCTTCT|1440|
|ATTTCGGATC|AACTGTATTG|ACTACATTGA|TCTTTTTTAA|CGAAGTTTAC|GACTTACTAA|1500|
|ATCCCCACAA|ACAAATCAAC|TGAGAAAA| | | |1528|

( 2 ) INFORMATION FOR SEQ ID NO:6:

( i ) SEQUENCE CHARACTERISTICS:
        ( A ) LENGTH: 341 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

| | | | | | | |
|---|---|---|---|---|---|---|
|CCAAGATAGG|CTATTTTGT|CGCATAAATT|TTTGTCTCGG|AGTGAAAACC|CCTTTTATGT|60|
|GAACAGATTA|CAGAAGCGTC|CTACCCCTCA|CCGGTTGAGA|TGGGAGAAA|ATTAAGCGAT|120|
|GAGGAGACGA|TTATTGGTAT|AAAAGAAGCA|ACCAAAATCC|CTTATTGTCC|TTTTCTGATC|180|
|AGCATCAAAG|AATATTGTCT|TAAAACGGGC|TTTTAACTAC|ATTGTTCTTA|CACATTGCAA|240|
|ACCTCTTCCT|TCTATTTCGG|ATCAACTGTA|TTGACTACAT|TGATCTTTTT|TAACGAAGTT|300|
|TACGACTTAC|TAAATCCCCA|CAAACAAATC|AACTGAGAAA|A| |341|

( 2 ) INFORMATION FOR SEQ ID NO:7:

( i ) SEQUENCE CHARACTERISTICS:
        ( A ) LENGTH: 19 base pairs ( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:7:

AAATTAAGCG ATGAGGAGA                       19

( 2 ) INFORMATION FOR SEQ ID NO:8:

( i ) SEQUENCE CHARACTERISTICS:
( A ) LENGTH: 1547 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:8:

| | | | | | |
|---|---|---|---|---|---|
| AATTCTTTTT | TTCAGACCAT | ATGACCGGTC | CATCTTCTAC | GGGGGGATTA | TCTATGCTTT | 60 |
| GACCTCTATC | TTGATTCTTT | TATGATTCAA | ATCACTTTTA | CGTTATTTAT | TACTTACTGG | 120 |
| TTATTTACTT | AGCGCCTTTT | CTGAAAAACA | TTTACTAAAA | ATCATACATC | GGCACTCTCA | 180 |
| AACACGACAG | ATTGTGATCA | AGAAGCAGAG | ACAATCACCA | CTAAGGTTGC | ACATTTGAGC | 240 |
| CAGTAGGCTC | CTAATAGAGG | TTCGATACTT | ATTTTGATAA | TACGACATAT | TGTCTTACCT | 300 |
| CTGAATGTGT | CAATACTCTC | TCGTTCTTCG | TCTCGTCAGC | TAAAAATATA | ACACTTCGAG | 360 |
| TAAGATACGC | CCAATTGAAG | GCTACGAGAT | ACCAGACTAT | CACTAGTAGA | ACTTTGACAT | 420 |
| CTGCTAAAGC | AGATCAAATA | TCCATTTATC | CAGAATCAAT | TACCTTCCTT | TAGCTTGTCG | 480 |
| AAGGCATGAA | AAAGCTACAT | GAAAATCCCC | ATCCTTGAAG | TTTTGTCAGC | TTAAAGGACT | 540 |
| CCATTTCCTA | AAATTTCAAG | CAGTCCTCTC | AACTAAATTT | TTTTCCATTC | CTCTGCACCC | 600 |
| AGCCCTCTTC | ATCAACCGTC | CAGCCTTCTC | AAAAGTCCAA | TGTAAGTAGC | CTGCAAATTC | 660 |
| AGGTTACAAC | CCCTCAATTT | TCCATCCAAG | GGCGATCCTT | ACAAAGTTAA | TATCGAACAG | 720 |
| CAGAGACTAA | GCGAGTCATC | ATCACCACCC | AACGATGGTG | AAAAACTTTA | AGCATAGATT | 780 |
| GATGGAGGGT | GTATGGCACT | TGGCGGCTGC | ATTAGAGTTT | GAAACTATGG | GGTAATACAT | 840 |
| CACATCCGGA | ACTGATCCCA | CTCCGAGATC | ATATGCAAAG | CACGTGATGT | ACCCCGTAAA | 900 |
| CTGCTCGGAT | TATCGTTGCA | ATTCATCGTC | TTAAACAGTA | CAAGAAACTT | TATTCATGGG | 960 |
| TCATTGGACT | CTGATGAGGG | GCACATTTCC | CCAATGATTT | TTTGGGAAAG | AAAGCCGTAA | 1020 |
| GAGGACAGTT | AAGCGAAAGA | GACAAGACAA | CGAACAGCAA | AAGTGACAGC | TGTCAGCTAC | 1080 |
| CTAGTGGACA | GTTGGGAGTT | TCCAATTGGT | TGGTTTTGAA | TTTTACCCA | TGTTGAGTTG | 1140 |
| TCCTTGCTTC | TCCTTGCAAA | CAATGCAAGT | TGATAAGACA | TCACCTTCCA | AGATAGGCTA | 1200 |
| TTTTTGTCGC | ATAAATTTTT | GTCTCGGAGT | GAAAACCCCT | TTTATGTGAA | CAGATTACAG | 1260 |
| AAGCGTCCTA | CCCTTCACCG | GTTGAGATGG | GGAGAAAATT | AAGCGATGAG | GAGAAAATTA | 1320 |
| AGCGATGAGG | AGACGATTAT | TGGTATAAAA | GAAGCAACCA | AAATCCCTTA | TTGTCCTTTT | 1380 |
| CTGATCAGCA | TCAAAGAATA | TTGTCTTAAA | ACGGGCTTTT | AACTACATTG | TTCTTACACA | 1440 |
| TTGCAAACCT | CTTCCTTCTA | TTTCGGATCA | ACTGTATTGA | CTACATTGAT | CTTTTTTAAC | 1500 |
| GAAGTTTACG | ACTTACTAAA | TCCCCACAAA | CAAATCAACT | GAGAAAA | | 1547 |

( 2 ) INFORMATION FOR SEQ ID NO:9:

( i ) SEQUENCE CHARACTERISTICS:
( A ) LENGTH: 360 base pairs ( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:9:

| | | | | | | |
|---|---|---|---|---|---|---|
| CCAAGATAGG | CTATTTTGT | CGCATAAATT | TTTGTCTCGG | AGTGAAAACC | CCTTTTATGT | 60 |
| GAACAGATTA | CAGAAGCGTC | CTACCCTTCA | CCGGTTGAGA | TGGGAGAAA | ATTAAGCGAT | 120 |
| GAGGAGAAAA | TTAAGCGATG | AGGAGACGAT | TATTGGTATA | AAGAAGCAA | CCAAAATCCC | 180 |
| TTATTGTCCT | TTTCTGATCA | GCATCAAAGA | ATATTGTCTT | AAAACGGGCT | TTAACTACA | 240 |
| TTGTTCTTAC | ACATTGCAAA | CCTCTTCCTT | CTATTTCGGA | TCAACTGTAT | TGACTACATT | 300 |
| GATCTTTTTT | AACGAAGTTT | ACGACTTACT | AAATCCCCAC | AAACAAATCA | ACTGAGAAAA | 360 |

( 2 ) INFORMATION FOR SEQ ID NO:10:

( i ) SEQUENCE CHARACTERISTICS:
( A ) LENGTH: 25 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:10:

GATAGGCTAT TTTTGTCGCA TAAAT    25

( 2 ) INFORMATION FOR SEQ ID NO:11:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: Other nucleic acid
( A ) DESCRIPTION: Synthetic DNA ( x i ) SEQUENCE DESCRIPTION: SEQ ID NO:11:

GAATTCACTA AGCGACTCAT CATC    24

( 2 ) INFORMATION FOR SEQ ID NO:12:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: Other nucleic acid
( A ) DESCRIPTION: Synthetic DNA ( x i ) SEQUENCE DESCRIPTION: SEQ ID NO:12:

GAATTCTCCG GAACTGATCC GACT    24

( 2 ) INFORMATION FOR SEQ ID NO:13:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: Other nucleic acid
( A ) DESCRIPTION: Synthetic DNA ( x i ) SEQUENCE DESCRIPTION: SEQ ID NO:13:

GAATTCTCAT TGGACTCTGA TGAG                                                                  24

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Synthetic DNA ( x i ) SEQUENCE DESCRIPTION: SEQ ID NO:14:

GAATTCCAGC TGTCAGCTAC CTAG                                                                  24

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Synthetic DNA ( x i ) SEQUENCE DESCRIPTION: SEQ ID NO:15:

GAATTCCCAA GTAGGCTATT TTTG                                                                  24

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Synthetic DNA ( x i ) SEQUENCE DESCRIPTION: SEQ ID NO:16:

GAATTCTACA GAAGCGTCCT ACCC                                                                  24

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Synthetic DNA ( x i ) SEQUENCE DESCRIPTION: SEQ ID NO:17:

GAATTCGTTG AGATGGGGAG AAAA                                                                  24

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Synthetic DNA ( x i ) SEQUENCE DESCRIPTION: SEQ ID NO:18:

GAATTCCGAT TATTGGTATA AAAG                                                                                          24

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: Synthetic DNA (xi) SEQUENCE DESCRIPTION: SEQ ID NO:19:

TTCGAAGTTT TTCTCAGTTG ATTT                                                                                          24

(2) INFORMATION FOR SEQ ID NO:20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: Synthetic DNA (xi) SEQUENCE DESCRIPTION: SEQ ID NO:20:

AATTCGATAG GCTATTTTG TCGCATAAAT G                                                                                   31

(2) INFORMATION FOR SEQ ID NO:21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: Synthetic DNA (xi) SEQUENCE DESCRIPTION: SEQ ID NO:21:

AATTCATTTA TGCGACAAAA ATAGCCTATC G                                                                                  31

(2) INFORMATION FOR SEQ ID NO:22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: Synthetic DNA (xi) SEQUENCE DESCRIPTION: SEQ ID NO:22:

CCGGATCCAC TAAGCGAGTC ATCATC                                                                                        26

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: Synthetic DNA (xi) SEQUENCE DESCRIPTION: SEQ ID NO:23:

CCGAATTCGA CAATATTCTT TGATGC    26

(2) INFORMATION FOR SEQ ID NO:24:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: Other nucleic acid
    (A) DESCRIPTION: Synthetic DNA (xi) SEQUENCE DESCRIPTION: SEQ ID NO:24:

GAATTCCCAA GATAGGCTAT TTTTG    25

(2) INFORMATION FOR SEQ ID NO:25:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: Other nucleic acid
    (A) DESCRIPTION: Synthetic DNA (xi) SEQUENCE DESCRIPTION: SEQ ID NO:25:

TTCGAAGTTT TTCTCAGTTG ATTTGTTTGT GGGGAT    36

(2) INFORMATION FOR SEQ ID NO:26:

(i) SEQUENCE CHARACTERISTICS:
    (A) LENGTH: 50 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:26:

TTGATAAGAC ATCACCTTCC AAGATAGGCT ATTTTGTCG CATAAATTTT    50

(2) INFORMATION FOR SEQ ID NO:27:

(i) SEQUENCE CHARACTERISTICS:
    (A) LENGTH: 30 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:27:

CCAAGATAGG CTATTTTTGT CGCATAAATT    30

(2) INFORMATION FOR SEQ ID NO:28:

(i) SEQUENCE CHARACTERISTICS:
    (A) LENGTH: 29 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:28:

TGCTGATAGC CTAACGTTCA TGATCAAAA    29

(2) INFORMATION FOR SEQ ID NO:29:

(i) SEQUENCE CHARACTERISTICS:
    (A) LENGTH: 32 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:29:

AAGCGATAGA GAGACTGCGC TAAGCATTAA TG   32

(2) INFORMATION FOR SEQ ID NO:30:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: Other nucleic acid
    (A) DESCRIPTION: Synthetic DNA (xi) SEQUENCE DESCRIPTION: SEQ ID NO:30:

GAATTCCCAA GATAGGCTAT TTTTG   25

(2) INFORMATION FOR SEQ ID NO:31:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: Other nucleic acid
    (A) DESCRIPTION: Synthetic DNA (xi) SEQUENCE DESCRIPTION: SEQ ID NO:31:

TTCGAAGTTT TTCTCAGTTG ATTTGTTTGT GGGGAT   36